United States Patent
Flom et al.

[11] Patent Number: 6,048,309
[45] Date of Patent: Apr. 11, 2000

[54] SOFT TISSUE RETRACTOR AND DELIVERY DEVICE THEREFOR

[75] Inventors: James R. Flom, Palo Alto; Meir Moshe, El Sobrante; Stephen W. Boyd, San Mateo; Richard L. Mueller, Byron, all of Calif.

[73] Assignee: Heartport, Inc., Redwood City, Calif.

[21] Appl. No.: 08/934,426

[22] Filed: Sep. 19, 1997

Related U.S. Application Data

[63] Continuation-in-part of application No. 08/610,619, Mar. 4, 1996, Pat. No. 5,810,721.

[51] Int. Cl.[7] .................................................. A61B 17/02
[52] U.S. Cl. ........................ 600/234; 600/206; 600/208; 600/227; 600/231
[58] Field of Search .................................... 600/234, 233, 600/235, 229, 228, 201, 206, 208, 215, 226, 227, 231

[56] References Cited

U.S. PATENT DOCUMENTS

| | | |
|---|---|---|
| 1,810,466 | 6/1931 | Deutsch . |
| 2,070,670 | 2/1937 | Marshall ................................ 600/234 |
| 2,305,289 | 4/1942 | Coburg . |
| 2,739,587 | 9/1956 | Scholl . |
| 3,111,943 | 11/1963 | Orndorff . |
| 3,332,417 | 7/1967 | Blanford et al. . |
| 3,347,226 | 10/1967 | Harrower . |
| 3,347,227 | 10/1967 | Harrower . |
| 3,397,692 | 8/1968 | Creager, Jr. et al. . |
| 3,523,534 | 8/1970 | Nolan . |
| 3,841,332 | 10/1974 | Treacle . |
| 3,863,639 | 2/1975 | Kleaveland ............................ 600/208 |
| 4,155,355 | 5/1979 | Yamamoto ............................ 600/234 |
| 4,188,975 | 2/1980 | Wenander . |
| 4,274,398 | 6/1981 | Scott, Jr. . |
| 4,412,532 | 11/1983 | Anthony . |
| 4,421,107 | 12/1983 | Esters et al. .......................... 600/234 |
| 4,430,991 | 2/1984 | Darnell . |
| 4,434,791 | 3/1984 | Darnell . |
| 4,492,229 | 1/1985 | Grunwald . |
| 4,553,537 | 11/1985 | Rosenberg . |
| 4,562,832 | 1/1986 | Wilder et al. . |
| 4,726,356 | 2/1988 | Santilli et al. ......................... 600/234 |
| 4,777,943 | 10/1988 | Chvapil . |
| 5,005,108 | 4/1991 | Pristash et al. . |

(List continued on next page.)

OTHER PUBLICATIONS

Robinson, et al., "Minimally Invasive Coronary Artery BypassGrafting: A New Method Using an AnteriorMediastinotomy," *J. Card. Surg.*, 1995; 10:529–536.

Landreneau, et al., "Video–Assisted Thoracic Surgery: Basic Technical Concepts and Intercostal Approach Strategies," *Ann. Thoracic Surg.*, 1992; 54:800–7.

Information Sheet Referencing "LoneStar Retractor System".

Information Sheets Referencing "Vi–Drape" Surgical Drape.

*Primary Examiner*—Paul J. Hirsch
*Attorney, Agent, or Firm*—Jens E. Hoekendijk; Jeffry J. Grainger

[57] ABSTRACT

The present invention provides a retractor for providing surgical access through a passage in a patient's body, together with a delivery device for positioning the retractor in the patient's body. The retractor comprises an anchoring frame having an upper surface, a lower surface, and an opening therethrough which defines an axial axis. A flexible tensioning member is attached to the frame, and is extendable from the frame out of the body through the passage when the frame is positioned through the passage and into a body cavity. The retractor is held by the delivery device in a collapsed orientation for placement in the patient's body. The delivery device is released from the retractor to allow the retractor to assume an expanded orientation in the patient's body. This tensioning member is selectively tensionable to spread the tissue radially outwardly from the axial axis.

37 Claims, 22 Drawing Sheets

U.S. PATENT DOCUMENTS

| | | | |
|---|---|---|---|
| 5,052,374 | 10/1991 | Alvarhez-Jacinto | 600/234 |
| 5,159,921 | 11/1992 | Hoover . | |
| 5,213,114 | 5/1993 | Bailey, Jr. | 600/208 |
| 5,231,974 | 8/1993 | Giglio et al. . | |
| 5,263,922 | 11/1993 | Sova et al. . | |
| 5,351,680 | 10/1994 | Jung . | |
| 5,366,478 | 11/1994 | Brinkerhoff et al. . | |
| 5,391,156 | 2/1995 | Hildwein et al. . | |
| 5,441,044 | 8/1995 | Tovey et al. | 600/234 |
| 5,452,733 | 9/1995 | Sterman et al. . | |
| 5,460,170 | 10/1995 | Hammerslag . | |
| 5,520,610 | 5/1996 | Giglio et al. . | |
| 5,520,611 | 5/1996 | Rao et al. . | |
| 5,524,644 | 6/1996 | Crook . | |
| 5,582,577 | 12/1996 | Lund et al. . | |
| 5,613,751 | 3/1997 | Parker et al. . | |
| 5,618,096 | 4/1997 | Parker et al. . | |
| 5,681,341 | 10/1991 | Lunsford et al. | 600/208 |

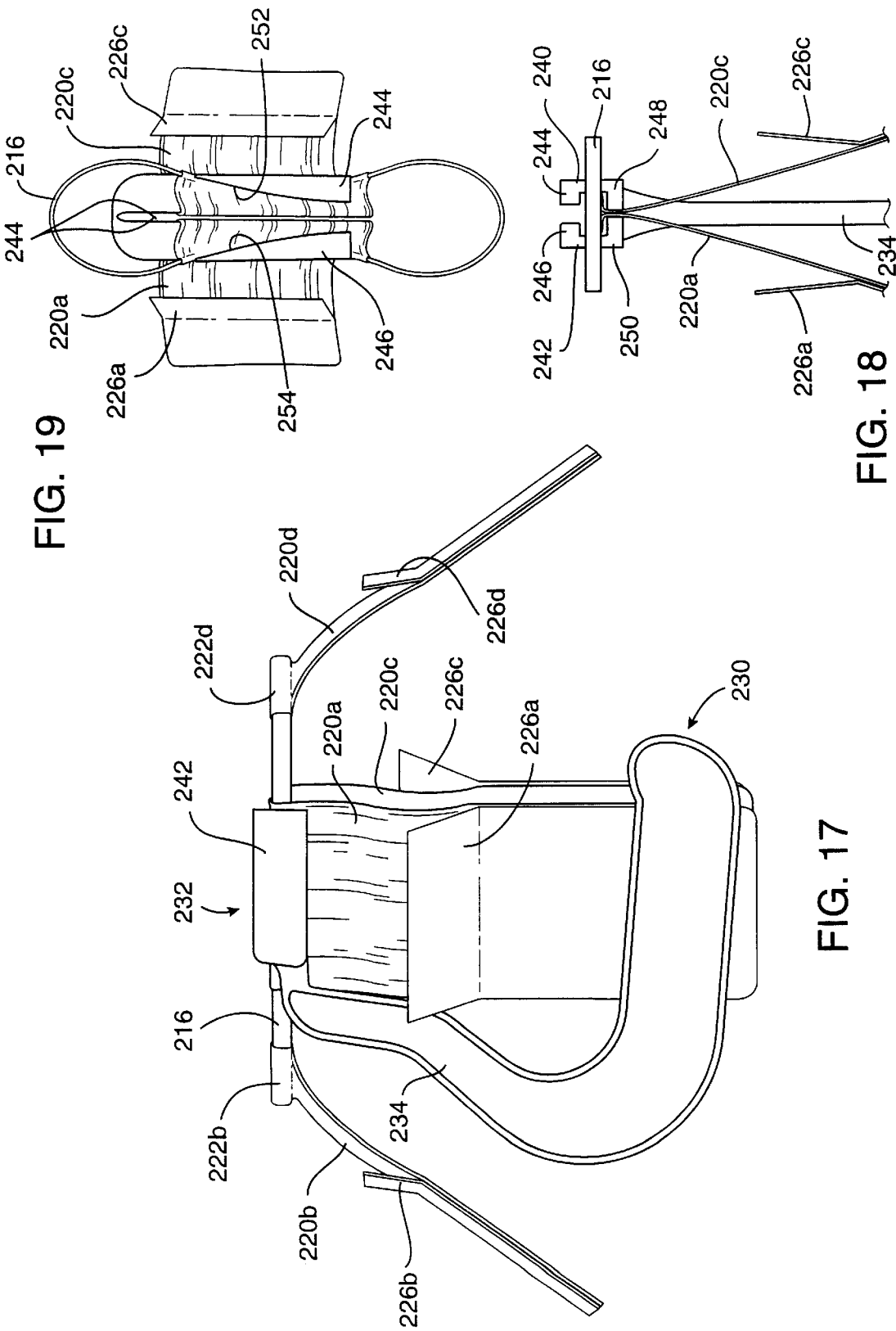

SOFT TISSUE RETRACTOR AND DELIVERY DEVICE THEREFOR

CROSS-REFERENCE TO RELATED APPLICATIONS

This application is a continuation-in-part and division of application Ser. No. 08/610,619, filed Mar. 4, 1996 now U.S. Pat. No. 5,810,721 and entitled SOFT TISSUE RETRACTOR AND METHOD FOR PROVIDING SURGICAL ACCESS.

BACKGROUND OF THE INVENTION

1. Field of the Invention

The present invention relates generally to minimally invasive and less invasive surgical access. More particularly, the present invention provides retractors for soft tissues, as well as delivery devices and methods for using the retractors to provide surgical access into body cavities.

Coronary artery disease remains the leading cause of morbidity and mortality in western societies. Coronary artery disease is manifested in a number of ways. For example, disease of the coronary arteries can lead to insufficient blood flow resulting in the discomfort and risks of angina and ischemia. In severe cases, acute blockage of coronary blood flow can result in myocardial infarction, leading to immediate death or damage to the myocardial tissue.

A number of approaches have been developed for treating coronary artery disease. In less severe cases, it is often sufficient to treat the symptoms with pharmaceuticals and lifestyle modification to lessen the underlying causes of disease. In more severe cases, the coronary blockage can often be treated endovascularly using techniques such as balloon angioplasty, atherectomy, or stents.

In cases where pharmaceutical treatment and/or endovascular approaches have failed or are likely to fail, it is often necessary to perform a coronary artery bypass graft procedure using open surgical techniques. Such techniques require that the patient's sternum be opened and the chest be spread apart to provide access to the heart. A source of arterial blood is then connected to a coronary artery downstream from an occlusion, while the patient's heart is maintained under cardioplegia and circulation is supported by cardiopulmonary bypass. The source of blood may be a vessel taken from elsewhere in the body such as a saphenous vein or radial artery, or an artery in the chest or abdomen such as the left or right internal mammary artery or the gastroepiploic artery. The target coronary artery can be the left anterior descending artery, right coronary artery, circumflex artery, or any other coronary artery which might be narrowed or occluded.

While very effective in many cases, the use of open surgery to perform coronary artery bypass grafting is highly traumatic to the patient. The procedure requires immediate post-operative care in an intensive care unit, a total period of hospitalization of seven to ten days, and a recovery period that can be as long as six to eight weeks.

Recently, it has been proposed to utilize minimally invasive surgical techniques and procedures to perform coronary artery bypass grafting and other traditionally open-chest cardiac surgical procedures. A wide variety of laparoscopic, arthroscopic, endovascular, and other minimally invasive surgical therapies have been developed. These procedures generally utilize trocars, cannulas, catheters, or other tubular sheaths to provide an artificial lumen, through which specialized tools are inserted and manipulated by the surgeon.

An exemplary minimally invasive bypass method is described in U.S. Pat. No. 5,452,733, assigned to the assignee of the present application, the full disclosure of which is herein incorporated by reference. This exemplary coronary artery bypass method relies on viewing the cardiac region through a thoracoscope and endovascularly portioning the patient's arterial system at a location within the ascending aorta. The bypass procedure is performed under cardiopulmonary bypass and cardioplegia, while the coronary anastomoses are formed within the chest cavity through the use of a plurality of trocar sheaths placed between the patient's ribs.

Although thoracoscopic methods hold great promise for decreasing morbidity and mortality, cost, and recovery time when compared to conventional open surgical coronary bypass procedures, these methods could benefit from still further improvements. In particular, the surgical access provided by known trocar sheaths has not been optimally adapted for performing thoracoscopic coronary artery bypass. The length of conventional trocar sheaths and the small size of their lumens limits the maneuverability of surgical instruments and inhibits the ability to look directly into the chest cavity while an instrument is positioned through the trocar sheath.

It would therefore be desirable to provide improved surgical access devices and methods for their use in performing less invasive coronary artery bypass grafting and other thoracoscopic surgical procedures, and minimally invasive surgical procedures in general. It would be particularly desirable if such devices and techniques provided atraumatic retraction of soft tissue of the chest wall to create the largest possible surgical access window without resorting to a sternotomy or gross retraction or removal of the ribs. Preferably, such improved surgical access devices and methods would provide a flexible access lumen which could be positioned and sized to meet the individual patient's physiology. The devices should have minimum height so as to extend as little as possible from the inner or outer surfaces of the chest wall. It would further be desirable if such access devices and methods allowed direct or magnified viewing of the internal procedure from outside the patient body, thereby decreasing the time and trauma associated with the internal surgical procedure, and increasing overall efficacy over both open surgical procedures and minimally invasive surgical procedures performed through the small trocar sheaths which have been relied on in the prior art.

2. Description of Background Art

Conventional thoracoscopic techniques are described in Landreneau et al. (1992) Ann. Thorac. Surg. 54:800–807. Conventional open surgical procedures for performing coronary artery bypass grafting are described in Kirkland and Barratt Boyes, Cardiac Surgery, John Wiley and Sons, Inc., New York, 1993 (2nd Ed.).

A minimally invasive method for performing coronary artery bypass grafting using an anterior mediastinotomy, including excision of either the third or fourth costal cartilage, is described by Robinson et al. in J. Card. Surg. (1995) 10:529–536.

U.S. Pat. No. 5,391,156 describes a flexible endoscopic surgical port having a tubular body, the outer end of which is optionally divisible into a plurality of flaps, thereby matching the length of the tubular body with the thickness of a body wall. A retainer ring engages the flaps to hold the port axially, while the hoop strength of the tubular body holds the adjacent tissue in a retracted position. U.S. Pat. No. 4,274,398 describes a surgical retractor having elastic tubes which hold hooks under radial tension from a notched frame. U.S. Pat. Nos. 4,430,991 and 4,434,791 describe similar surgical retractor frames for use with hooked members. Such a system is commercially available under the trade name LoneStar Retractor System™.

A surgical drape having a central open ring for insertion over known surgical retractors is commercially available from Becton Dickinson of Franklin Lakes, N.J. under the tradename Vidrape®. Relevant minimally invasive methods and devices for heart surgery are described in U.S. Pat. No. 5,452,733, U.S. Pat. No. 5,571,215, U.S. Pat. No. 5,501,698, U.S. Pat. No. 5,588,949, and U.S. patent application Ser. No. 08/486,941, filed Jun. 7, 1995, which corresponds to PCT Application No. WO 96/40354 published Dec. 19, 1996, the full disclosures of which patents and application are incorporated herein by reference.

SUMMARY OF THE INVENTION

In a first aspect, the present invention provides a retractor for providing surgical access to a body cavity of a patient through a passage in tissue. The retractor comprises an anchoring frame having an upper surface, a lower surface, and an opening therethrough which defines an axial axis. The anchoring frame is positionable through the passage into the body cavity. A flexible tensioning member is attached to the anchoring frame and extendable from the frame out of the body through the passage. The tensioning member is selectively tensionable to spread the tissue radially outwardly from the axial axis. Hence, it is the tension imposed on the flexible tensioning member which effects retraction of the tissue, rather than relying on the structural integrity of a tubular structure such as a trocar sheath.

Generally, an attachment mechanism on the tensioning member maintains tension so as to retract tissue from the passage. Hence, the tensioning member need only be capable of withstanding and transferring the tension imposed by the attachment mechanism, there being no need for a rigid structure having sufficient hoop strength to maintain the tissue in the retracted position. The resulting surgical access window need not be compromised by any rigid lumen wall or rigid blade-type structure, and the retraction load is distributed atraumatically over a wide area of the tissue by the flexible tensioning member.

Preferably, the anchoring frame will have a narrow profile configuration for insertion through an incision into the body cavity, and will be expandable to a wide profile configuration once inside the body cavity. The frame may comprise a variety of collapsible and expandable structures, including a ring of resilient material which expands to the large configuration when released. The tensioning member is preferably formed of a plurality of elongate tabs or strips of cloth, tape, cord, or strap material, ideally comprising an absorbent material such as gauze so as to absorb any fluids released by the tissue bordering the passage. Alternatively, an elastomeric or semi-elastomeric sheet or strip may be used.

In another aspect, the present invention provides a retractor for providing surgical access into a chest cavity defined by a plurality of ribs. The ribs are separated by intercostal tissue and an intercostal width. The retractor comprises an anchoring frame which is insertable into the chest cavity through a passage between two ribs, the frame having an opening. A flexible tensioning member extends from at least two opposing sides of the opening in the frame. The tensioning member is able to extend out of the chest cavity through the passage when the frame is within the chest cavity and the opening in the frame is generally aligned with the passage. The tensioning member may be tensioned to spread the intercostal tissue outward toward the two ribs. Such a retractor is particularly well suited for forming an anterior mediastinotomy or small thoracotomy for use in a less invasive coronary artery bypass grafting procedure or other cardiac procedure.

Generally, an attachment mechanism on the tensioning member maintains outward radial tension from outside the patient to hold the intercostal tissue in a retracted position. In some embodiments, the attachment mechanism comprises an adhesive disposed on the tensioning member to facilitate attachment to an outer surface of the patient's chest. Optionally, a surgical film may be adhered to the exterior of the chest surrounding the passage to facilitate adherence of the tensioning member to the chest wall. In alternative embodiments, the attachment mechanism comprises a plurality of clasps or other coupling devices disposed about an outer ring structure which is positioned outside the body cavity.

In yet another aspect, the present invention provides an illuminated retractor for providing surgical access to a body cavity of a patient through a passage in tissue. The retractor comprises an internal anchor having an opening, the anchor being insertable through the passage and into the body cavity. A tissue restraining structure extends proximally from the internal anchor for holding the passage open sufficiently to provide direct visualization of the internal body cavity from outside the patient. Typically, an external anchor is spaced proximally from the internal anchor on the tissue restraining member. An illuminating device is disposed adjacent to the opening in the internal anchor to facilitate visualization of the cavity through the open passage.

The present invention also provides a method for retracting tissue to temporarily widen a penetration into a body cavity, the method comprising positioning an anchoring frame against a tissue surface within the body cavity adjacent to the penetration so that an opening in the frame is aligned with the penetration. The frame has a width across the opening which is wider than the penetration. A tissue restraining member extending from the frame out of the body cavity through the penetration is tensioned so as to urge the tissue adjacent the penetration outwardly.

In a further aspect, the present invention provides a method for performing surgery on a patient's heart, the heart being disposed within a chest cavity defined by a plurality of ribs, the ribs being separated by intercostal tissue and an intercostal width. The method comprises inserting an anchoring frame into the chest cavity through an incision between two ribs, wherein the frame has an opening and a width across the opening wider than the intercostal width. Tension is then imposed on a plurality of flexible tabs extending from the frame adjacent to the opening so as to widen the incision. Surgery is then performed on the heart using instruments positioned through the widened incision.

The present invention also provides a tissue retractor system for providing surgical access through an incision in tissue to a body cavity of a patient. The system generally comprises a retractor and a retractor delivery device. Specifically, the retractor comprises an anchoring frame having an opening, wherein the frame is restrainable into a narrow profile to facilitate insertion of the frame into the body cavity. The frame is expandable into a wide profile when inside the body cavity. A flexible tensioning member extends from the frame adjacent to the opening and is selectively tensionable to retract the tissue adjacent the incision, and is adapted to be secured in tension outside the body cavity.

The retractor delivery device of the invention comprises in one embodiment a handle and a retractor engaging portion including first and second retractor engaging surfaces which hold the retractor in its narrow profile. The delivery device is used to position the retractor in a patient's body and is able to release the retractor to allow expansion of the retractor within the body.

In another embodiment, the retractor delivery device comprises a handle having an axis and a retractor engaging portion coupled to the handle, the retractor engaging portion being spaced from and generally parallel to the axis of the handle. The retractor engaging portion is coupled to the handle by a connecting member which extends transversely to the axis of the handle.

The invention also provides a sterilized medical kit comprising a retractor including an anchoring frame and at least one flexible tensioning member, and a device for placing the retractor in a patient's body, wherein the retractor and the device are contained in a sealed package and maintained in sterile condition.

The invention also provides a method for loading the retractor onto a delivery device adapted to deliver the retractor into an incision formed in a patient's body, as well as a method of positioning a retractor loaded onto a delivery device in a patient's body.

Other features, benefits and advantages of the invention will be apparent from the following description of preferred embodiments taken in conjunction with the accompanying drawing Figures.

BRIEF DESCRIPTION OF THE DRAWINGS

FIG. 14A is an end elevation view of the retractor engaging portion of the delivery device of FIG. 14.

FIG. 14B is a plan view of the retractor engaging portion of the delivery device shown in FIG. 14.

FIG. 17 is a side elevation view of the retractor system of FIG. 14, the retractor being fully loaded onto the delivery device.

FIG. 18 is an end elevation view of the retractor system of FIG. 17, with portions of the retractor omitted for clarity.

FIG. 19 is a top plan view of the retractor system of FIG. 17, with portions of the retractor removed for clarity.

DETAILED DESCRIPTION OF PREFERRED EMBODIMENTS

The devices and methods of the present invention are suitable for providing access for a variety of surgical procedures within the cavities of the body. Such access is particularly advantageous during minimally invasive and less invasive surgical procedures in which surgical instruments are introduced through an access window provided by the retraction of tissue.

The present retraction methods and devices will find particular use where direct visualization into a body cavity through a percutaneous penetration facilitates the surgical procedure. Alternatively, an endoscope, laparoscope, thoracoscope, or other visualization device may be inserted through such an access window for telescopic or video-based visualization. Additionally, tissues and/or organs may be temporarily extended through the access window to allow external manipulation during therapy. The retraction methods and devices of the present invention will thus find applications in providing surgical access to the pelvis, abdomen, thorax, and other body cavities, to facilitate surgical intervention on the gall bladder, colon, reproductive organs, kidneys, liver, stomach, heart, lungs, and other body structures.

The present invention will find its most immediate application in less-invasive surgery of the heart, particularly in less-invasive coronary artery bypass grafting, less-invasive valve repair and replacement, and other cardiac procedures. Surgical access windows provided by the flexible tensioning member of the retractor of the present invention will easily flex to adapt to the minimally invasive tools used in less invasive bypass procedures, thereby allowing these tools to be manipulated more easily and used at a wider range of angles than could be accommodated by the rigid and semi-rigid trocar sheaths and conventional rigid retractors of the prior art. By utilizing tension in a flexible strap or tab, the intercostal tissue between ribs may be atraumatically retracted as widely as possible without inflicting a gross displacement of the ribs and the resulting patient trauma. However, where greater access is desired and/or required, the retraction methods and devices of the present invention may also be used in combination with the excision of costal cartilage or even a partial sternotomy or small thoracotomy to maximize the size of the open access port.

Figure 1:
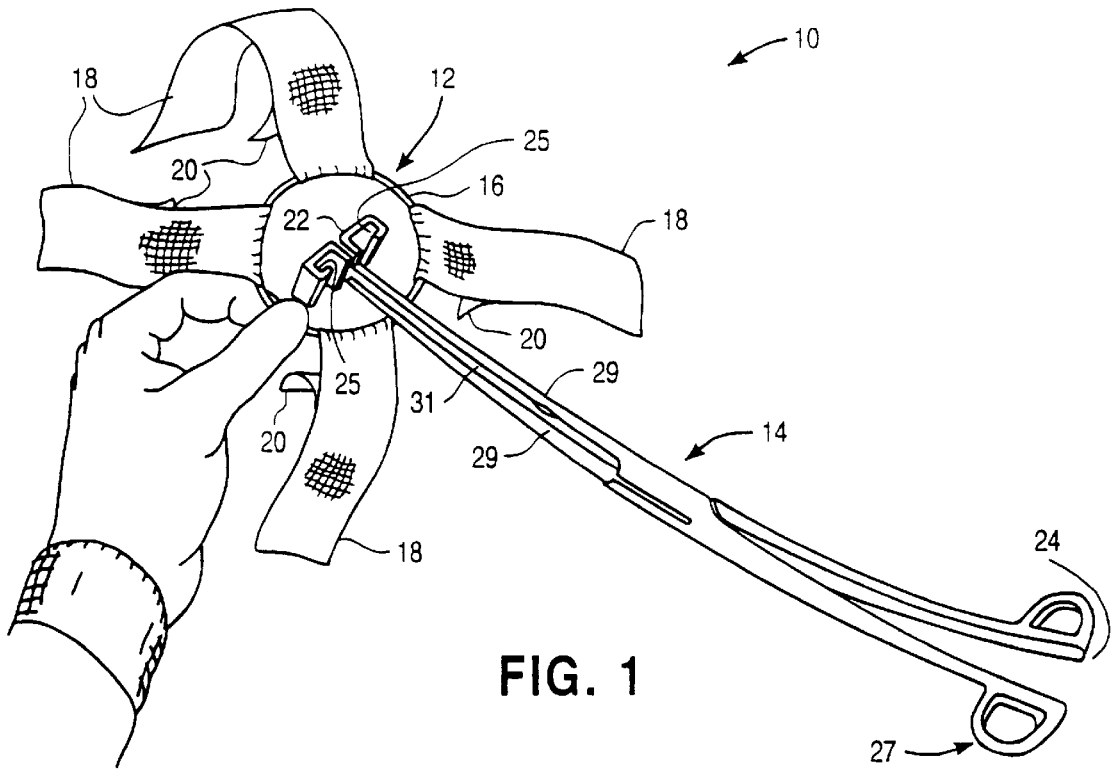
FIG. 1 illustrates a retractor system constructed according to one embodiment of the present invention, the system including a retractor and an associated delivery device.

Referring now to FIG. 1, a retraction system 10 comprises a retractor 12 and a delivery device 14. Retractor 12 includes an anchoring frame which is preferably in the form of an anchoring ring 16. A flexible tensioning member, and preferably a plurality of tensioning members, such as flexible tabs 18, extend from the ring 16. The flexible tabs 18 are provided with an attachment mechanism for maintaining tension on the members during retraction of tissue. A preferred attachment mechanism comprises an adhesive coated over a portion of each of the tabs 18. A backing strip 20 preferably removably covers the adhesive to facilitate handling the retractor.

Anchoring ring 16 may be either rigid or flexible, but preferably comprises a resilient material biased to form an annular ring shape. A variety of other frame shapes might also be used, including C-shaped, U-shaped, rectangular, elliptical, triangular and parabolic, such frame shapes optionally including articulated or living hinge joints. In any event, the anchoring frame will have at least two sections separated by an opening or gap such that the frame may be placed through a passage in a body wall into a body cavity and the two sections positioned on either side of the passage with the opening therebetween aligned with the passage. The anchoring ring 16 may optionally be made of a relatively high strength polymer such as Delrin™, nylon, high density polyethylene, and the like. Preferably, the anchoring ring 16 comprises a high strength biocompatible alloy, and preferably a superelastic alloy such as Nitinol. Such an alloy ring may be formed by welding, crimping the joint with a stainless steel tube, butt jointing with heat shrink tubing, or the like. The anchoring ring 16 preferably has a diameter between about 10 mm and 9 cm. The exemplary annular superelastic alloy anchoring ring 16 may be readily compressed to a small configuration for insertion into the body cavity, and will readily expand to the large open configuration shown in FIGS. 1–2 once inside the body cavity. The anchoring ring 16 is able to withstand the compressive loads imposed by flexible tabs 18 during retraction of tissue as described hereinbelow.

The axial dimension of anchoring ring 16 is preferably minimized to provide maximum open working area within the body cavity and to provide maximum maneuverability of instruments positioned through the ring. In an exemplary embodiment, the anchoring ring 16 has an axial thickness of less than about 20 mm, and preferably less than about 10 mm.

Flexible tabs 18 preferably comprise elongate strips of an absorbent material such as gauze, cloth tape, or the like. Such gauze tabs may be easily looped over anchoring ring 16 and sutured, sewn, adhesively bonded, heat sealed, or welded to themselves. Alternatively, tabs 18 may be directly adhesively bonded to anchoring ring 16, may be molded into the anchoring ring, or may have the anchoring ring woven into the tab material. Use of an absorbent material allows the flexible tab to absorb blood and other fluids which might otherwise seep from the retracted tissue into the body cavity. Where absorbency is less important, flexible tabs 18 may comprise an elastomer or a flexible, deformable or resilient metal.

The adhesive covered by backing strips 20 will generally comprise a medical grade adhesive suitable for attachment to human skin or to paper, cloth, metal or plastic surfaces, such as an acrylate or other suitable adhesive. Conveniently, attachment may be facilitated by the use of a plastic film adhered to the patient's chest prior to insertion of the retractor, allowing backing strips 20 to be affixed securely to the plastic film.

Delivery device 14 generally includes a distal end 22 and a proximal end 24. The distal end includes inward-facing surfaces 25 which releasably restrain the anchoring ring 16 in a small, collapsed configuration, while the proximal end 24 includes a handle 27 for manipulation of these inward-facing surfaces. Handle 27 preferably comprises a pair of finger loops which may be actuated by passing the thumb and a finger therethrough and separating and/or bringing together the thumb and finger. Arms 29 extend distally to support each of the inward-facing surfaces 25, the arms being hinged to form jaws 31 which widen or narrow the distance between inward-facing surfaces 25 as handle 27 is actuated. Preferably, arms 29 are generally U-shaped as shown, extending distally, turning outward, and returning proximally to inward-facing surfaces 25. Optionally, a releasable detent or ratchet (not shown) between the handles helps restrain inward-facing surfaces 25 at their closest proximity.

Figure 2:
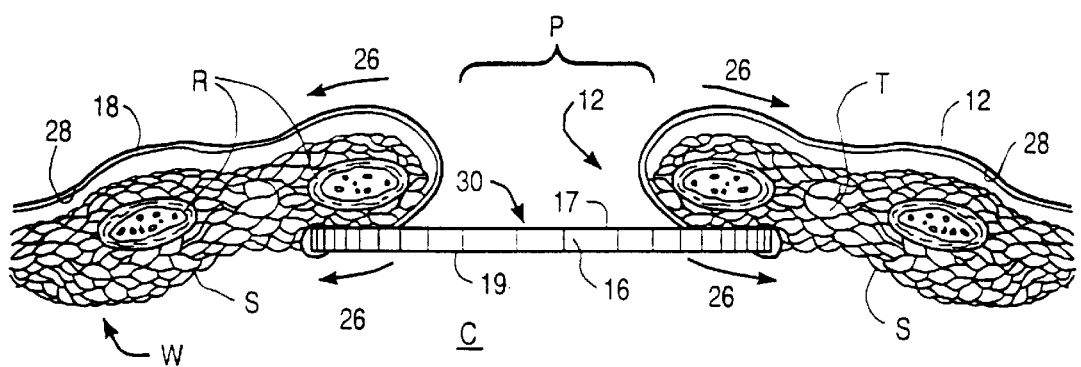
FIG. 2 is a cutaway view of the retractor of FIG. 1 as used for retracting intercostal tissue from between ribs to provide access to the chest cavity.

A particularly advantageous use of the retractor of FIG. 1 is for accessing the chest cavity by retracting the soft intercostal tissue between ribs and will be described with reference to FIG. 2. A chest wall W is defined by a plurality of ribs R separated by intercostal tissue T. The anchoring ring 16 of retractor 12 is shown inserted through a passage P through the chest wall. As used herein, a passage means any opening, puncture, wound or incision through tissue to a body cavity, whether open or closed. Hence, passage P may comprise an incision, a mediastinotomy, thoracotomy, or other opening formed by the cutting or removal of tissue, bone, or cartilage, a percutaneous opening through tissue, or the like. In any event, tabs 18 extend from the anchoring ring 16 outward through passage P. An upper surface 17 of anchoring ring 16 is placed against an inner surface S of chest wall W, while a lower surface 19 is oriented into the chest cavity C.

As tabs 18 are highly flexible and formed from separate elongate strips, they retract little or no tissue from the passage P when untensioned. However, when tension is applied to tabs 18, that tension is transmitted along the tab to act in a radial outward direction 26 against the tissue which borders the passage P. The transmission of tension through the flexible tabs results in a retraction of tissue from both outside and inside the body cavity, without interrupting the passage with a rigid trocar sleeve or other rigid retracting structure. Adhesive 28 disposed on tabs 18 conveniently allows the tissue to be held in the retracted position by affixing the tabs to the surface of the chest or to another external structure.

Access to the interior of body cavity C is thus provided through the passage P by retracting tissue so as to form an open window. Tabs 18 are radially opposed, so that opposing radial tensions 26 help to hold anchoring ring 16 in alignment with the open window, and also so that tissue is retracted in opposite directions. Thus, access to the body cavity is provided through an opening 30 in anchoring ring 16, which is preferably larger than the open passage to prevent any interference, and preferably wider than an intercostal width between adjacent, unretracted ribs.

Figure 2A:
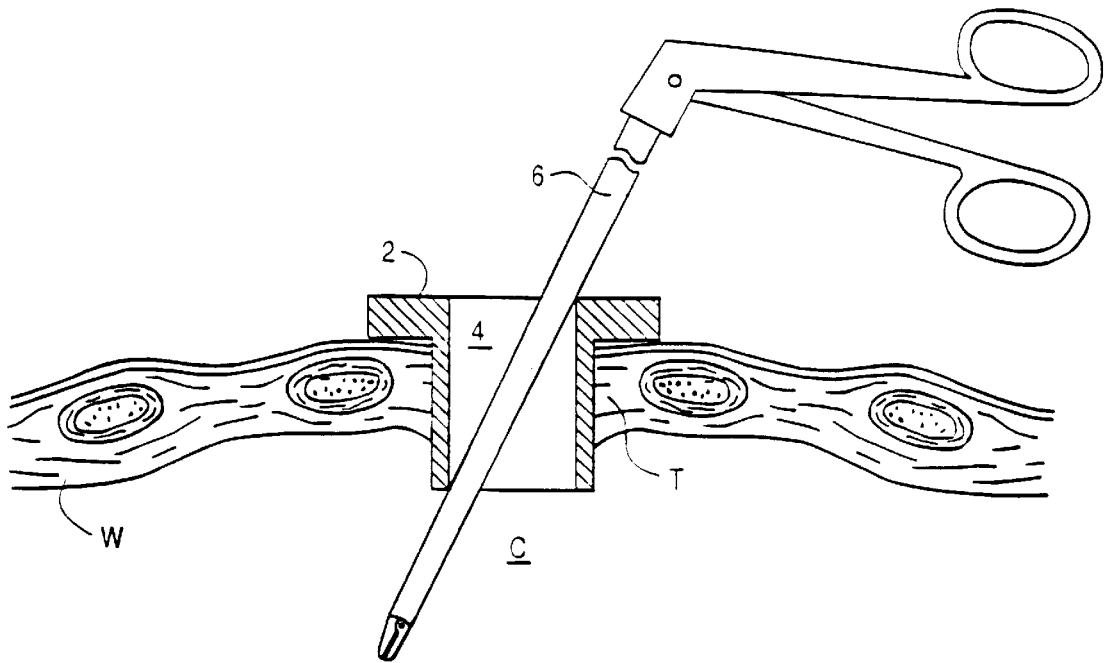
FIG. 2A is a cutaway view of a surgical instrument positioned through a typical known trocar sheath.
Figure 2B:
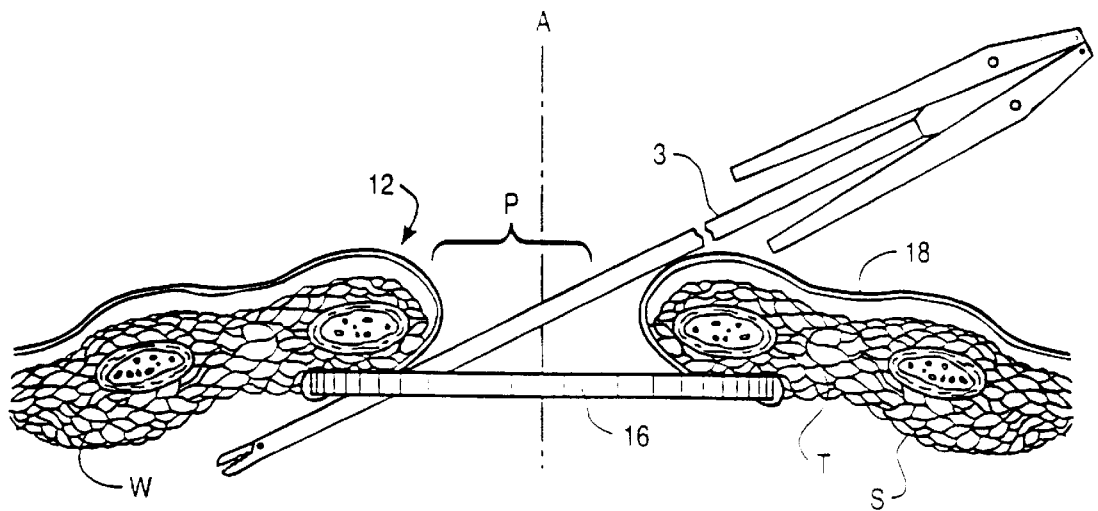
FIG. 2B is a cutaway view of a surgical instrument positioned through the retractor of FIG. 1, showing the increased angulation and maneuverability provided by the surgical access of the present invention.
Figure 3:
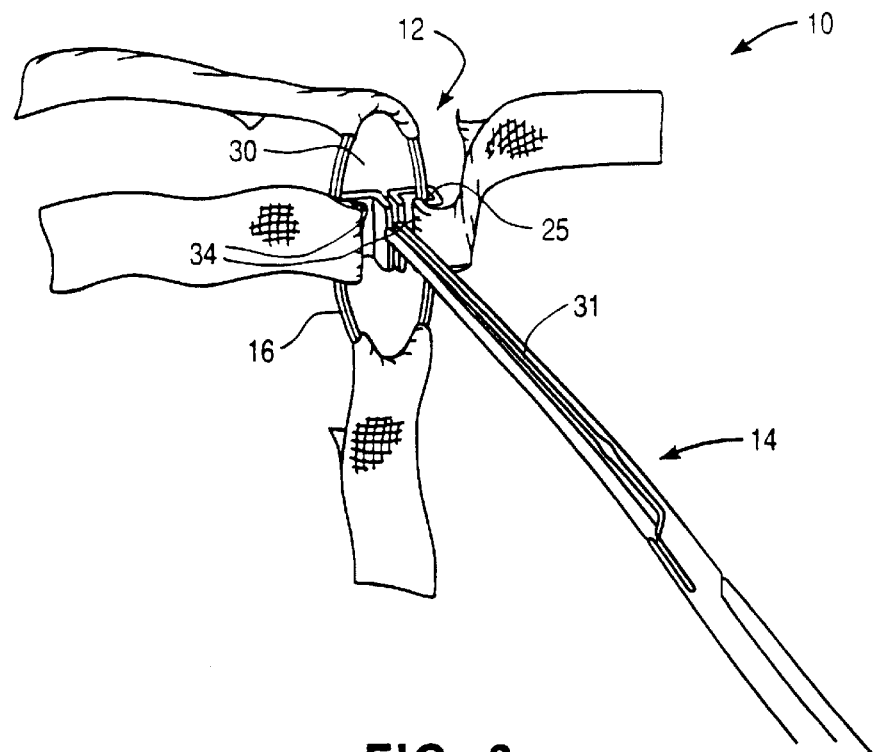
FIG. 3 illustrates the retractor system of FIG. 1 with the retractor restrained in a collapsed configuration by the delivery device.

The improved access and visualization provided by the retractor of the present invention is seen most clearly in FIGS. 2A and 2B. Conventional trocar sheath 2 has a structural lumen 4 which must have walls of sufficient rigidity and thickness to retract intercostal tissue T. The length of lumen 4 is significantly greater than the thickness of chest wall W to ensure that the lumen remains open when trocar sheath 2 is canted by a moderately angled surgical tool 6. The length of lumen 4 will also often be increased to allow trocar sheath 2 to accommodate chest walls of varying thickness, further decreasing unimpeded angulation and maneuverability of surgical tool 6. Clearly, direct visualization of an internal procedure through lumen 4 of trocar sheath 2 would be highly problematic, even where surgical tool 6 is limited to the moderate angle shown.

In contrast to known trocar sheaths, retractor 12 provides a surgical access window that accommodates less invasive surgical implement 3 at a large angle relative to axial axis A, and with improved maneuverability and visualization. Tension in tabs 18 retracts intercostal tissue T from passage P, and also pulls anchoring ring 16 firmly against the inner surface S of chest wall W. Not only does this avoid interference from the ring 16, but the tension of tabs 18 will actually compress the thickness of chest wall W adjacent passage P, further increasing the range of motion of implement 3. Finally, if even higher angles are required, the surgeon need only apply the force necessary to locally displace the tissue adjacent the angled tool, as the flexible tabs do not have a structural lumen which resists distortion. It can also be seen in FIG. 2B that visibility through a surgical access window provided by retractor 12 is substantially enhanced, particularly from viewpoints which are at a substantial angle from axial axis A of anchoring ring 16.

Figure 4:
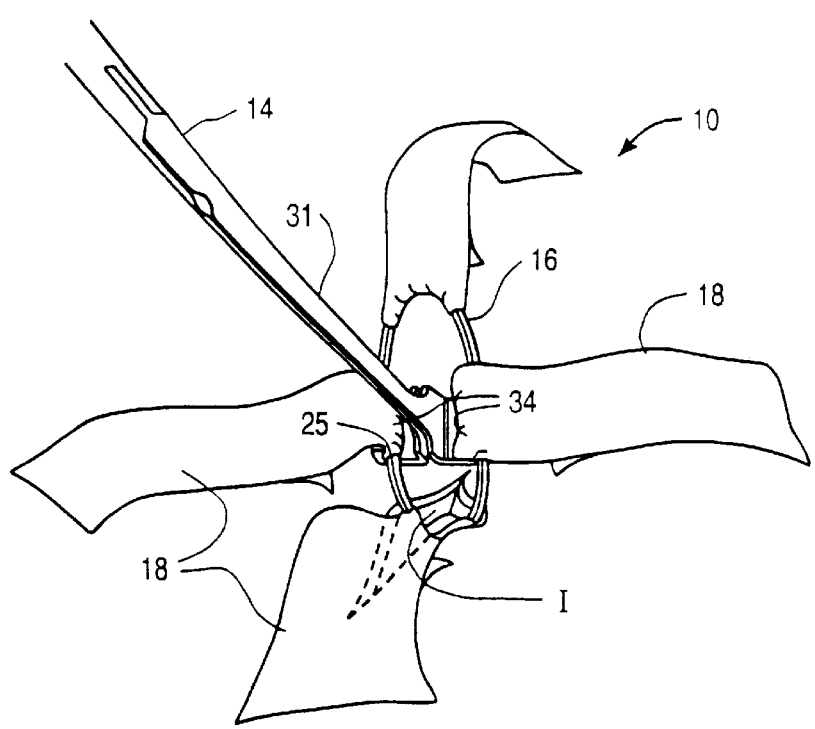
FIGS. 4–6 illustrate a method of using the retractor system of FIG. 1 to provide surgical access to a body cavity.

The deployment of retractor 12 using delivery device 14 will be explained with reference to FIGS. 3–6. Preferably, delivery device 14 is inserted through opening 30 and jaws 31 are opened to align channels 34 with anchoring ring 16. The anchoring ring 16 is positioned within channels 34 adjacent to inward-facing surfaces 25. The handle is then manipulated so that inward-facing surfaces 25 engage the anchoring ring 16 to squeeze the ring into the elongate, collapsed narrow profile configuration shown in FIGS. 3 and 4. Typically, delivery device 14 will releasably maintain the anchoring ring 16 in the narrow profile configuration during positioning. Anchoring ring 16 is then inserted through incision I, preferably in an edgewise orientation as shown in FIG. 4. As used herein, an edgewise orientation means that the axial axis of anchoring ring 16 is at an angle substantially less than 90° relative to, and preferably parallel to, the surface of the body on which incision I is disposed.

Figure 4A:
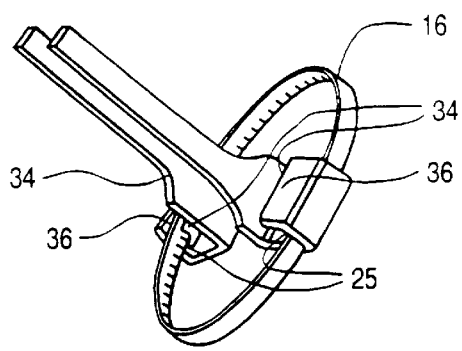
Figure 5:
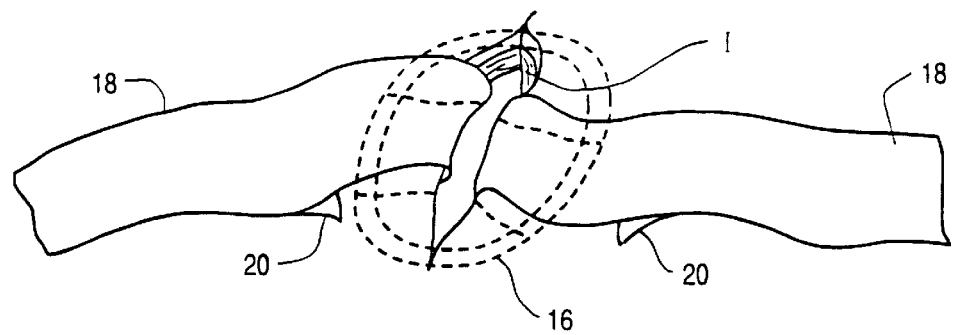

Release of anchoring ring 16 within the body cavity is most clearly understood with reference to FIGS. 4A and 5. As shown in FIG. 4A, the anchoring ring 16 may be expanded radially within the body cavity by moving inward-facing surfaces 25 away from one another. The delivery device 14 is withdrawn by first displacing it distally beyond detent 36. Jaws 31 are then closed and the delivery device 14 is withdrawn from the incision I.

Figure 6:
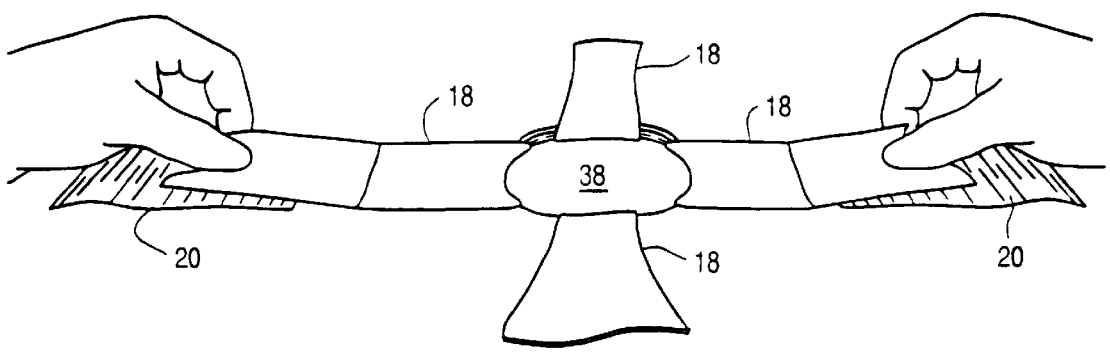

Prior to tensioning, opposed tabs 18 have little effect on the incision 1. Conveniently, the tabs may be simply pulled outward by hand to tension tabs 18 and thereby retract the tissue adjacent to the incision. Anchoring ring 16 is drawn into engagement with the interior surface S of the chest wall (as best seen in FIG. 2). When the tissue is sufficiently retracted, backing strips 20 are removed and the tabs affixed in place using the exposed adhesive, as illustrated in FIG. 6. The resulting open window 38 is of maximum size without any significant retraction of the ribs to accommodate various types and sizes of instruments and facilitate a high degree of angulation and motion of such instruments. Furthermore, the chest wall tissue is compressed between the tabs 18 and ring 16, which minimizes chest wall thickness to enhance instrument maneuverability. This is in contrast to conventional tubular ports, trocar sleeves, and other rigid retractors which have a significant length extending both into and outside of the body cavity, hampering manipulation of instruments.

Figure 6A:
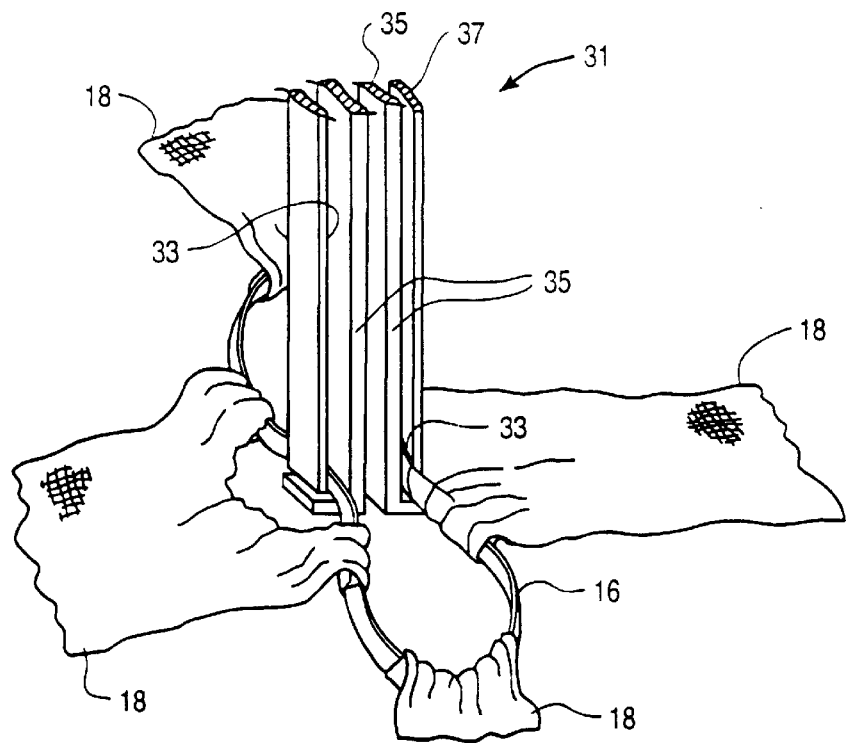
FIGS. 6A–6C illustrate alternative embodiments of delivery devices for use with the retractor of FIG. 1.
Figure 6B:
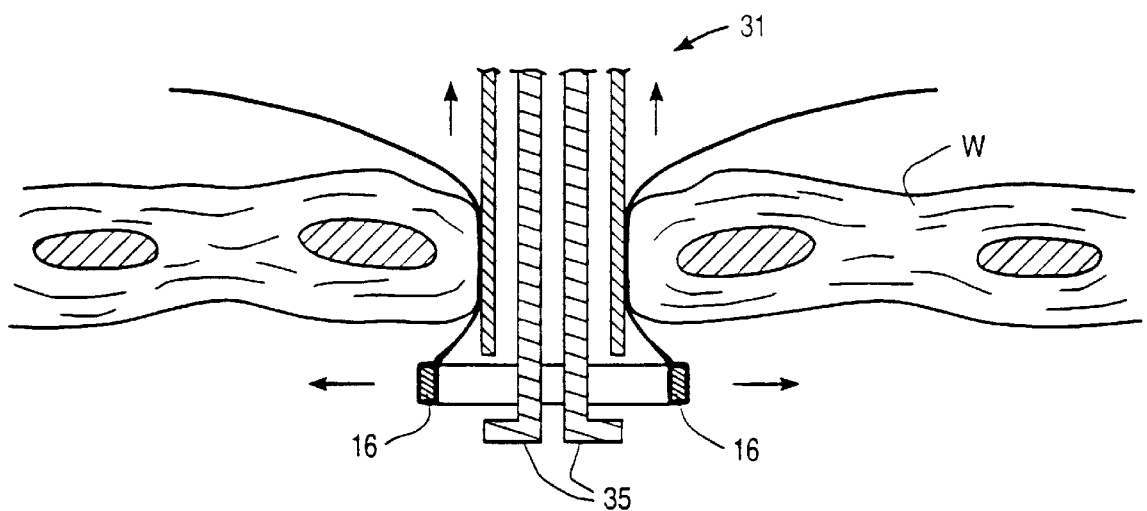

Referring now to FIGS. 6A and 6B, an alternative delivery device 31 includes an inner support member 35 and a slidable outer member 37 having inward-facing surfaces 33. Outer member 37 may be retracted proximally relative to an inner support member 35 to allow anchoring ring 16 to expand resiliently when released. The inner support member is then withdrawn from the expanded ring 16. A portion of tab 18 adjacent one of the inward-facing surfaces 33 is removed from FIG. 6A for clarity.

Figure 6C:
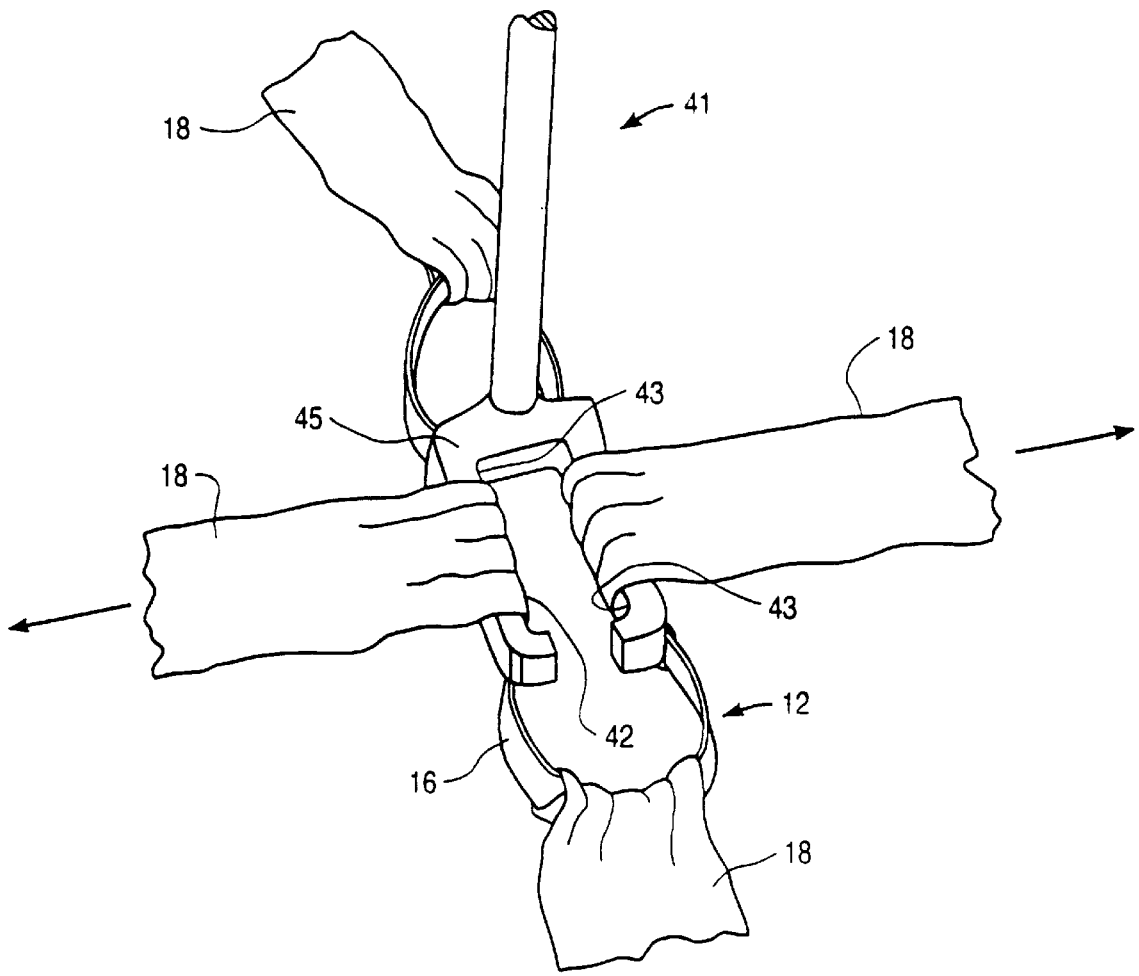
Figure 6G:
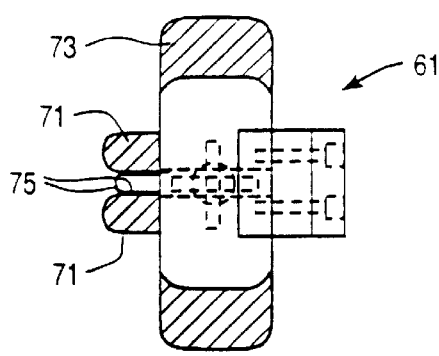
FIGS. 6D–6G illustrate an alternative embodiment of a retractor having grommets and an associated delivery device, according to the principles of the present invention.
Figure 6D:
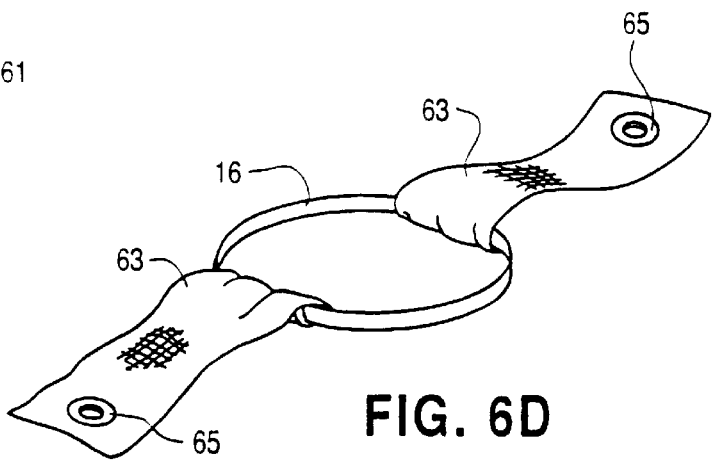
Figure 6F:
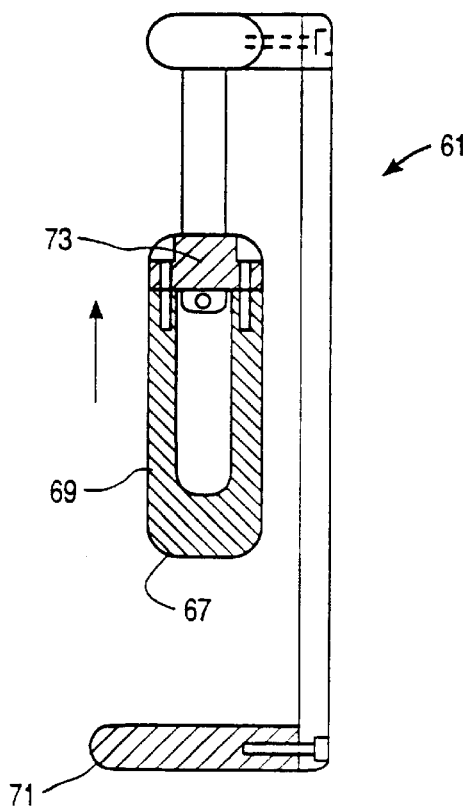
Figure 6E:
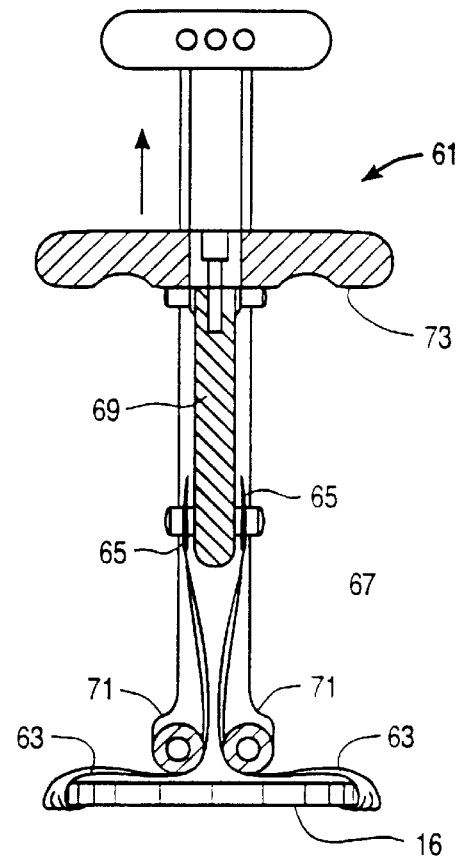

Referring now to FIG. 6C, a still further alternative delivery device 41 includes fixed inward-facing surfaces 43 on a distal bracket 45. Fixed surfaces 43 are defined by a slot 47 in bracket 45, the slot accepting a pair of opposing tabs 18. Tensioning of the tabs 18 which pass through slot 47 collapses anchoring ring 16 to the narrow profile configuration during insertion. Releasing the tension from outside the patient allows the anchoring ring 16 to expand resiliently.

A still further alternative delivery device 61 will be described with reference to FIGS. 6D–G. This embodiment makes use of a retractor having tabs 63 with openings which are reinforced with grommets 65. The grommets facilitate holding the tabs on pins 67 of actuator 69. The actuator is upwardly slidable relative to a pair of rollers 71 mounted to a handle 73. Tabs 63 are threaded around rollers 71 and grommets 65 placed over pins 67. As seen most clearly in the front view of FIG. 6F, grasping handle 73 and drawing the actuator in the upward direction indicated will tension the tabs and compress ring 16. Rollers 71 may optionally rotate, or the tabs may slide over the roller's rounded surface. In either case, the distance between the rollers need not change. Hence, the portion of each roller which is adjacent to the other roller defines an inward-facing roller surface 75; and the anchoring ring is restrainable in the narrow configuration by these inward-facing roller surfaces when the tab is held under tension by pin 67. Alternatively, the grommets maybe disposed on separate tethers attached to the ring, so that the tabs are used only for retraction of tissue.

Figure 7:
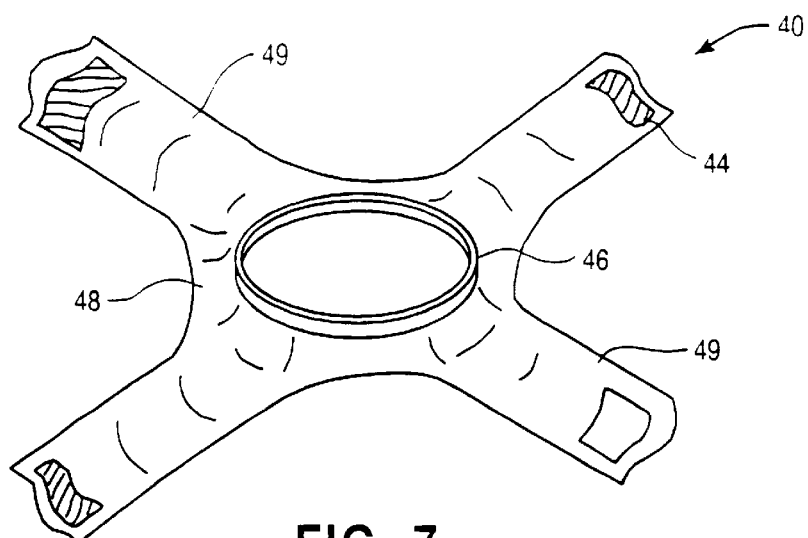
FIGS. 7–9A illustrate alternative embodiments of tissue retractors according to the principles of the present invention.

Referring now to FIG. 7, an alternative embodiment of a retractor according to the principles of the present invention comprises an internal anchoring ring 46 and a tissue restraining member comprising a single-piece sheet 48, which may be flat, bowl-shaped or tubular. The sheet 48 preferably comprises a thin semi-elastic polyethylene or urethane material. Adhesive backing 44 disposed on opposed extended tabs 49 provides an attachment mechanism to restrain the tissue in the retracted position.

Figure 8:
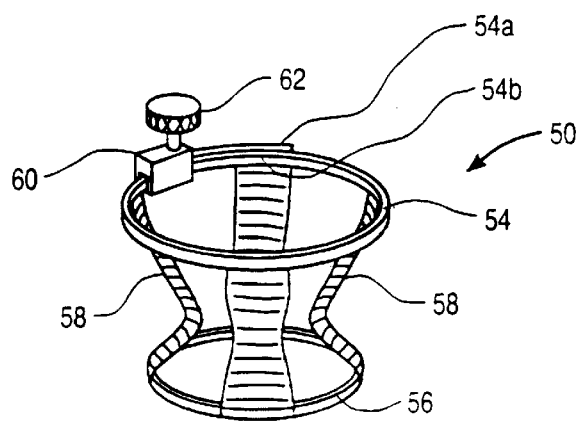

Referring now to FIG. 8, a still further alternative embodiment of the present retractor 50 comprises an outer ring 54, an anchoring ring 56, and tabs 58 coupled therebetween.

Expansion mechanism 60 allows the diameter of outer ring 54 to be increased when knob 62 is turned, thereby tensioning tabs 58 when the anchor ring is in position. In an exemplary configuration, outer ring 54 is a split ring with overlapping portions 54a, 54b. Expansion mechanism 60 comprises a clamp for clamping overlapping portions 54a, 54b in position; for example, knob 62 may be a set screw which engages overlapping portion 54a and urges it against portion 54b. Alternatively, expansion mechanism 60 may mechanically expand ring 54, for example, by a pinion gear attached to knob 62 which engages a series of teeth along one of overlapping portions 54a, 54b so as to expand ring 54 when the knob is turned.

Figure 9:
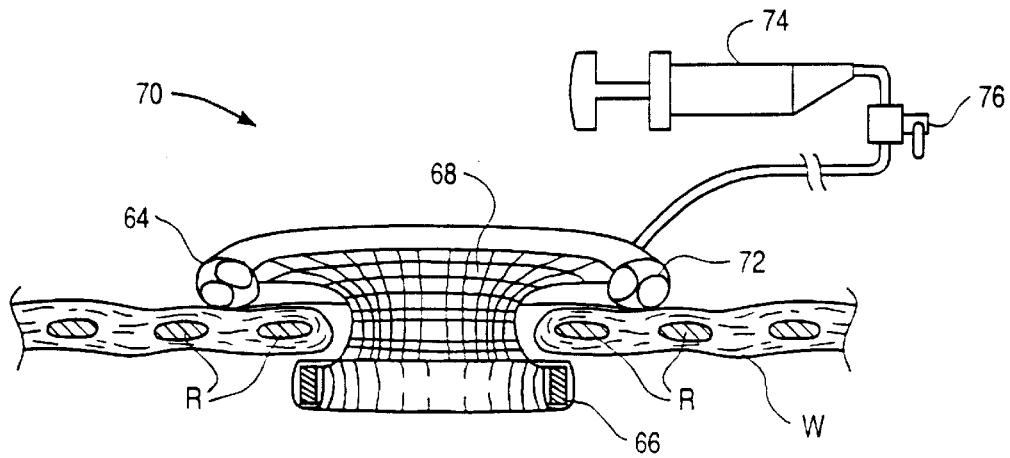

In a further embodiment, shown in FIG. 9, a balloon retractor 60 includes an outer balloon ring 64, an anchoring ring 66, and a tubular elastomeric tissue restraining member 68 extending therebetween, as seen in FIG. 9, for retracting tissue in chest wall W. Balloon ring 64 is generally elastomeric or semi-elastomeric, and preferably comprises baffles 72 to give the balloon greater structural integrity and stiffness. The size of the balloon ring (and hence the tension on restraining member 68) may be varied using inflation pump 74 and temporarily fixed with stopcock 76. As the diameter of the balloon ring expands under greater inflation pressure, the member 68 increasingly retracts tissue between ribs R.

Figure 9A:
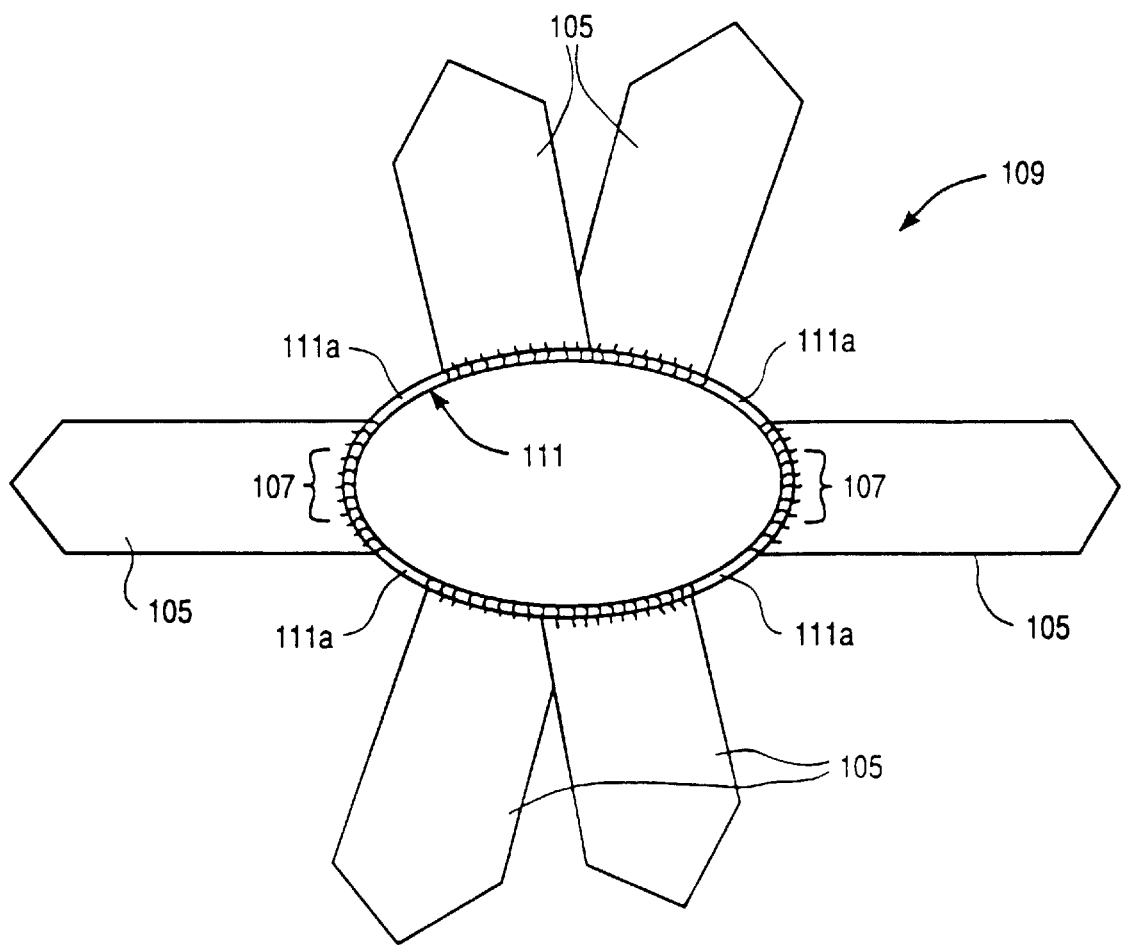

Referring now to FIG. 9A, a still further embodiment of the present invention comprises a retractor 109 including a polymeric anchoring ring 111 and a plurality of adhesive backed flexible tabs 105. Polymeric anchoring ring 111 includes rigid sections 111A separated by opposed living hinges 107, preferably formed by locally tapering the thickness of the ring material. Optionally, the anchoring ring is machined from nylon, Delrin™, a high density polyethylene, or another relatively high strength polymer. The living hinges 107 facilitate compressing the retractor into a narrow diameter configuration by promoting localized bending, and adhesive backed tabs 105 may optionally be attached to the ring by wrapping the tab about the ring so that the tab adhesive adheres to the ring surface. The living hinges 107 may alternatively comprise pin joints or other hinges to provide pivotal motion between sections 111A.

Figure 10A:
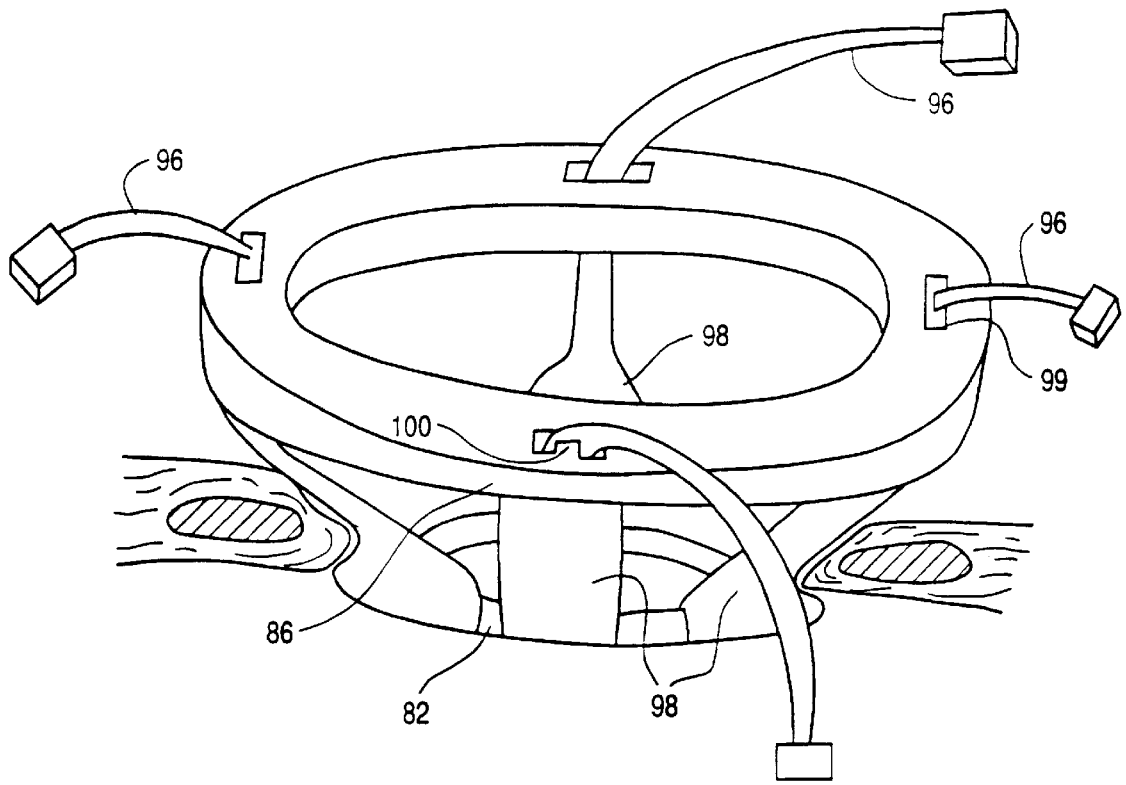
FIGS. 10A–10E illustrate an alternative embodiment of a retractor system according to the principles of the present invention and a method for its use.

Referring now to FIG. 10A, a still further embodiment of the present retractor 81 comprises an anchoring ring 82, tabs 84, and an outer ring 86. Tabs 84 have a tissue restraining portion 98 from which tethers 96 extend. Tethers 96 pass through slots 99 in outer ring 86, the tethers tensioning tissue restraining portions 98 so as to retract tissue from the passage. Conveniently, slots 99 are provided with catches, clamps, or ratchets 100 to engage each tether 96 so as to restrain the tissue in the retracted position. These ratchets facilitate expansion of the access window by manually pulling tethers 96 relative to outer ring 86.

Referring now to FIGS. 10B–10E, a particularly advantageous retractor system 80 comprises a retractor 81 and a delivery device including an obturator 88 having a longitudinal channel 89 with inward-facing surfaces 90 which restrain the anchoring ring therebetween. An actuation handle 92 is located on the proximal portion of the delivery device.

Once the obturator has been inserted through the chest wall W. depressing button 94 of handle 92 advances a push rod 95 distally to expel anchoring ring 82 distally from the obturator. The individual length of tabs 84 is selected to promote alignment between the anchoring ring opening and the passage through the tissue. Tabs 84 again include a tissue restraining portion 98 from which tethers 96 extend. Tethers 96 initially extend from tabs 84 through slots 99 in outer ring 86, and back to the proximal handle 92 of the delivery device. Thus, proximally retracting obturator 88 relative to the outer ring 86 pulls anchoring ring 82 against chest wall W and tensions tethers 96. Tethers 96 are attached to proximal handle 92 by anchors 101 which are held within apertures 103 in proximal handle 92, as shown in FIG. 10D. Rotation of knob 98 of proximal handle 92 releases anchors 101 from apertures 103 to decouple tethers 96 therefrom, allowing the delivery device to be removed from the retractor, leaving an open access port through the retractor as shown in FIG. 10A.

Figure 10F:
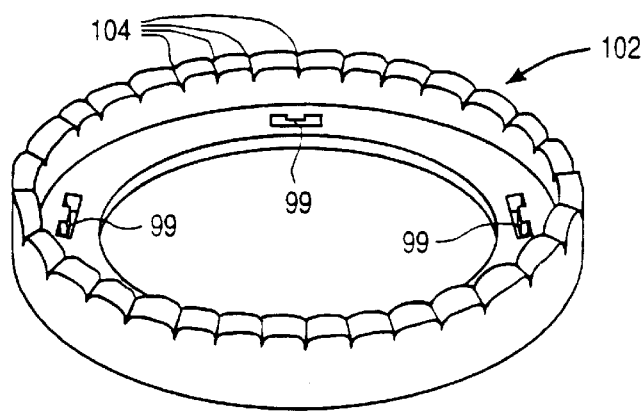
FIG. 10F illustrates an alternative outer ring structure for use with the retractor system of FIG. 10A.
Figure 10B:
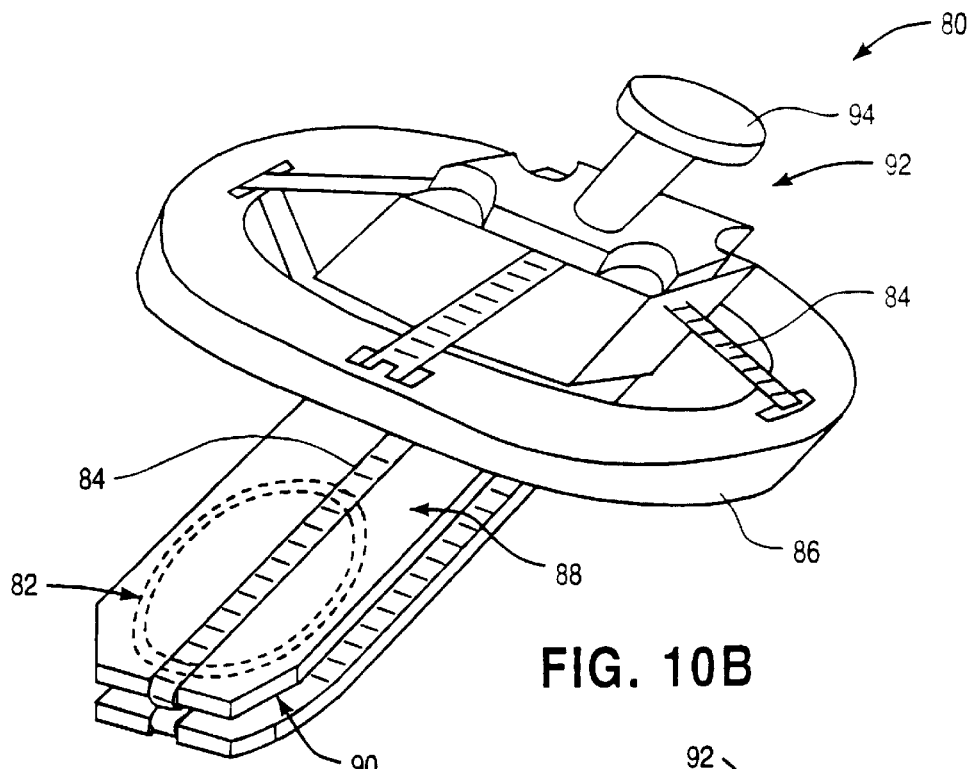
Figure 10C:
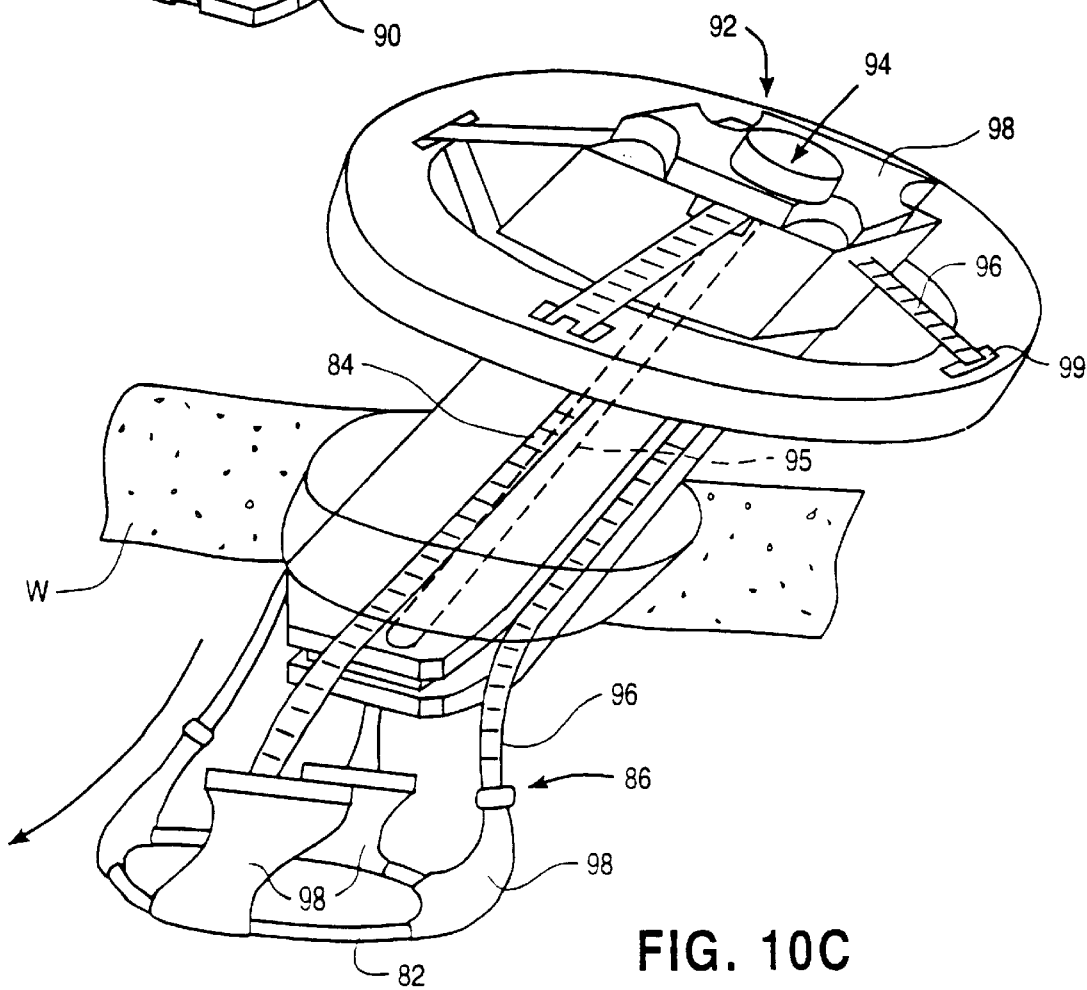
Figure 10D:
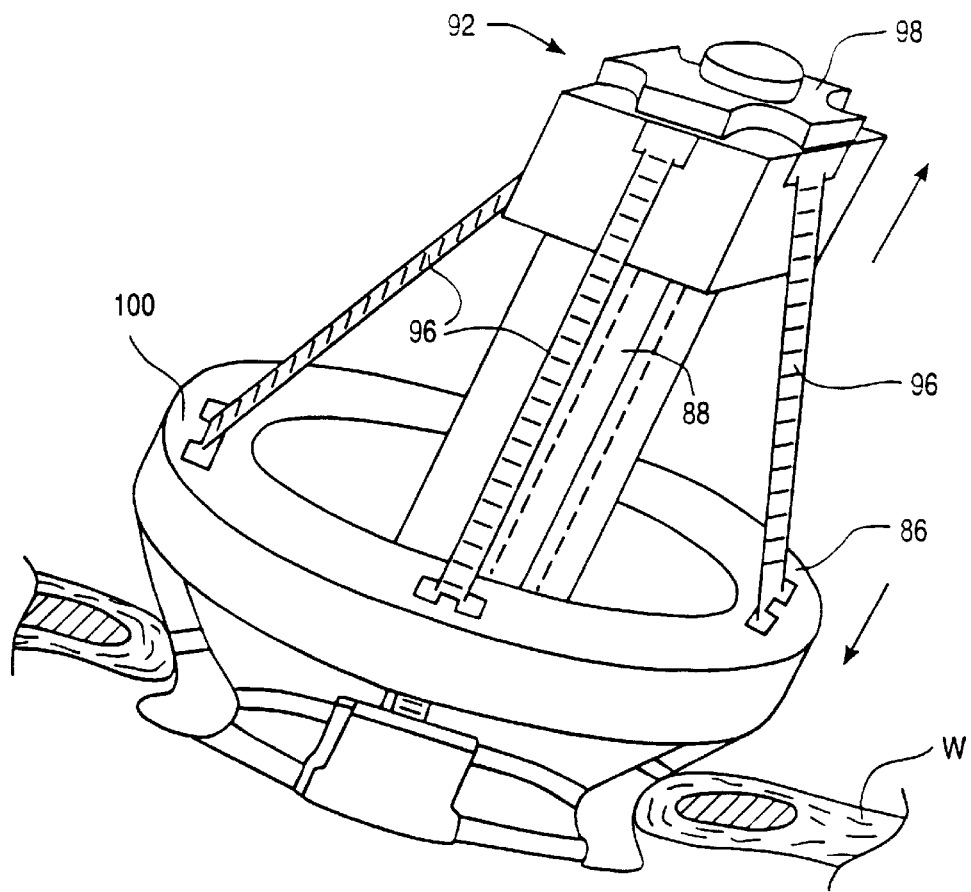
Figure 10E:
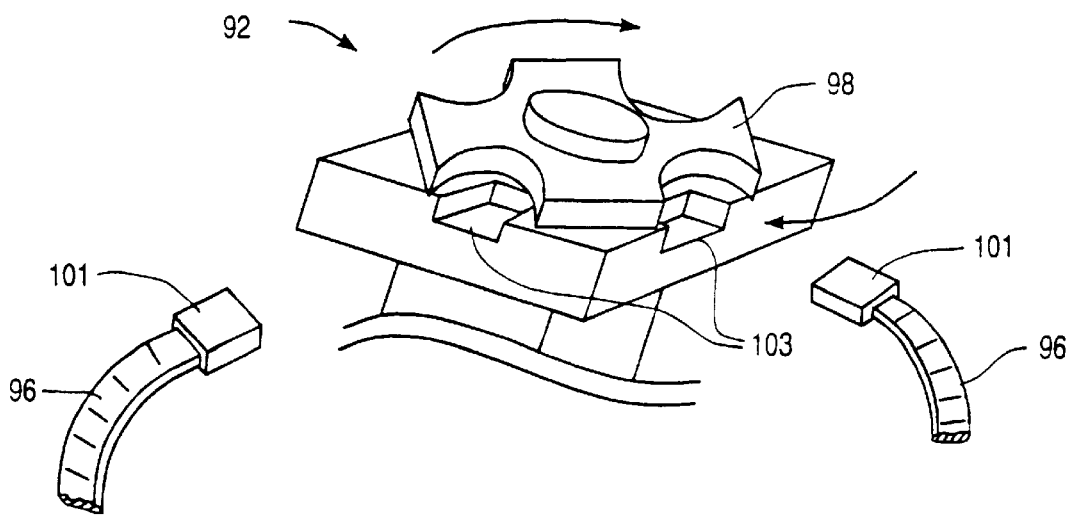

Referring now to FIG. 10F, an alternative outer ring 102 includes a plurality of temporary suture retainers 104 useful in maintaining suture organization in surgical procedures that require a large number of sutures. Retainers 104 may comprise a plurality of radially-oriented slots between 4 and 30 in number which are configured to frictionally retain a suture thread placed in the slot. Alternatively, retainers 104 may be hooks, eyelets, clamps, cleats, or the like.

Figure 11A:
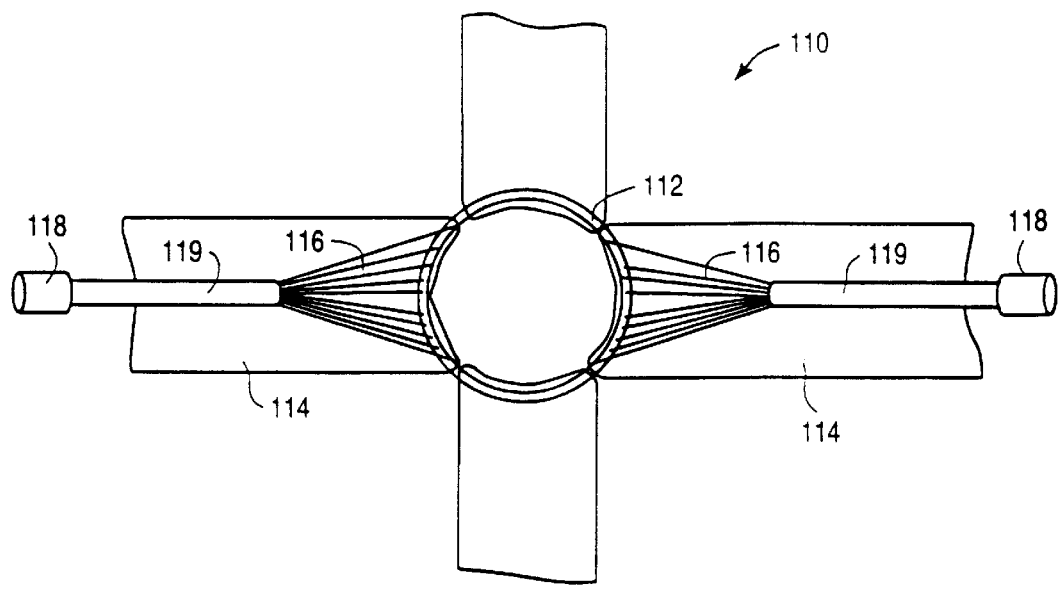
FIGS. 11A and 11B illustrate a retractor having illuminating fiberoptics disposed about an internal anchoring ring to provide both illumination and access to an internal body cavity, according to another embodiment of the present invention.
Figure 11B:
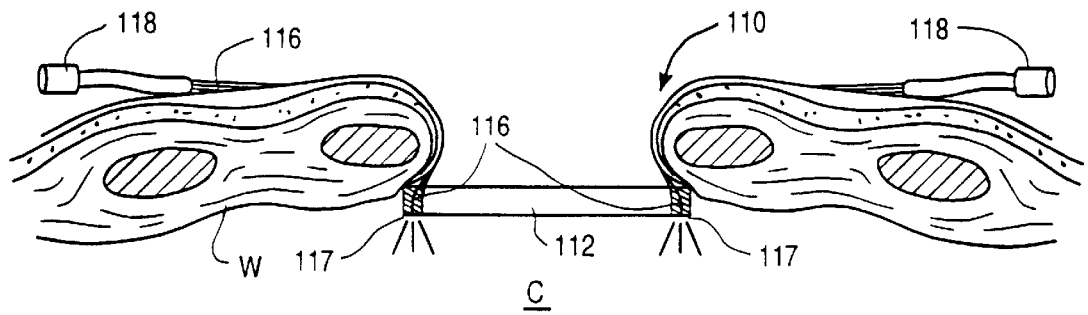

The retractors of the present invention are particularly advantageous when used with direct visualization through an open window, resulting in faster and more cost efficient less invasive surgical procedures. Such direct visualization reduces or avoids the necessity to resort to thoracoscopes and other remote imaging modalities. However, this elimination of the scope from the interior body cavity may also eliminate the primary source of illuminating light, the illumination fiberoptics which are generally provided with such scopes. Therefore, the present invention further provides illuminated retractors, an exemplary embodiment being illustrated in FIGS. 11A and 11B.

Illuminating retractor 110 includes an anchoring ring 112 and a plurality of tabs 114 as described above, and also includes a plurality of illuminating optical fibers 116 disposed about the anchoring ring 112 and having distal ends 117 pointing distally into the body cavity from the lower surface of the anchoring ring. Advantageously, optical fibers 116 extend independently in the proximal direction along the tabs 114, minimizing any reduction in the size of the opening in the body wall. These independent fibers are then combined together in a cable 119 a short distance from ring 112 and attached to one or more optical couplers 118. Cables 119 may or may not be mounted to one or more of tabs 114.

The illuminating ends 117 of optical fibers 116 are generally oriented distally into the body cavity, and may be molded into the anchoring ring 112, bonded onto an inner or outer surface of the anchoring ring, or may terminate along tabs 114 adjacent to the anchoring ring. Similarly, the dispersed fiberoptics along tabs 114 might be woven into a textile tab, imbedded within a polymer tab with reinforcing or malleable members for optimal light positioning, or be bonded onto an inner or outer surface of the tab. Advantageously, the dispersion of the optical fibers across the tab not only minimizes the profile of the fibers, but also helps to maintain the flexibility of the tabs.

Figure 12A:
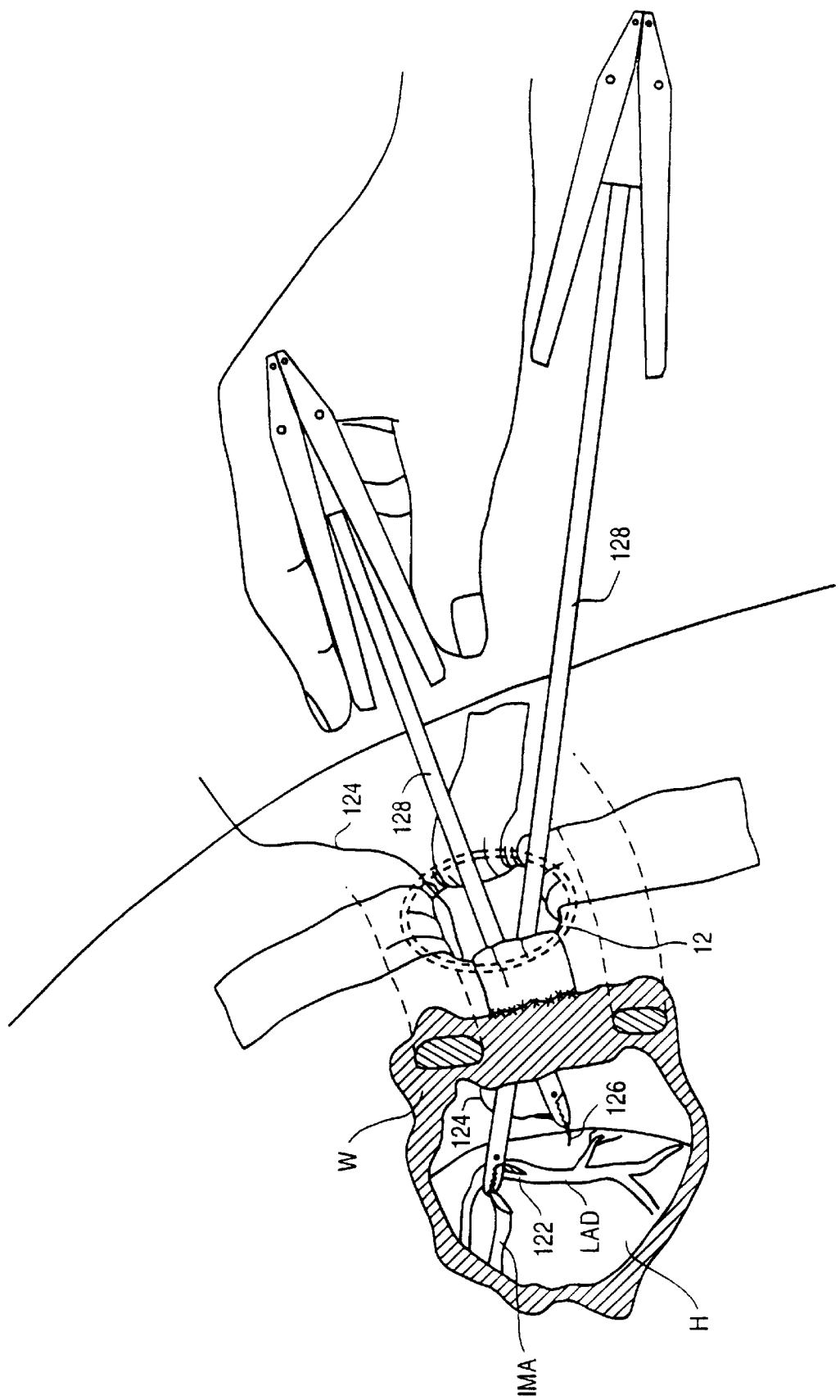
FIGS. 12A and 12B illustrate a method for using the retractor of FIG. 1 for coronary artery bypass grafting, according to one embodiment of the present invention.
Figure 12B:
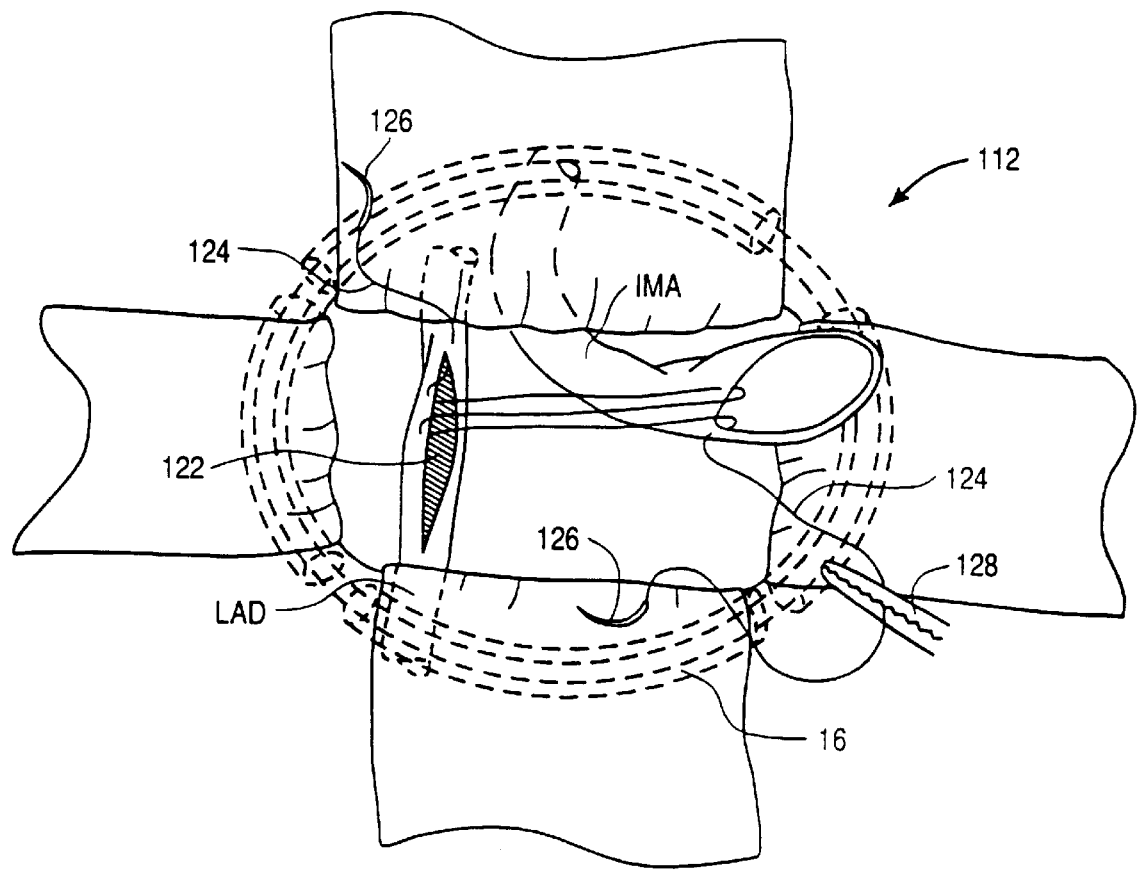

The use of retractor 12 during a coronary artery bypass grafting procedure is illustrated in FIGS. 12A and 12B. As more fully explained in U.S. Pat. No. 5,452,733, previously incorporated herein by reference, an exemplary bypass procedure involves harvesting of the internal mammary artery IMA and joining it with the diseased coronary artery, here the left anterior descending coronary artery LAD. Optionally, a plurality of conventional trocar sheaths may be used in combination with the retractor 12 of the present invention. Alternatively, the present method for coronary artery bypass grafting may be performed entirely through surgical access windows provided by one or more retractors according to the present invention.

Internal mammary artery IMA may be joined to incision 122 in the coronary artery LAD by a variety of conventional techniques, including suturing, laser welding, tissue gluing, microstapling, and the like. When conventional suturing techniques are used, a length of suture 124 having a needle 126 on at least one end may be manipulated using forceps 128 either inside the chest cavity, or outside the chest cavity directly adjacent retractor 12. In either case, forming the anastomoses is greatly facilitated by the high degree of instrument mobility and direct visualization of the procedure provided by retractor 12.

Figure 13:
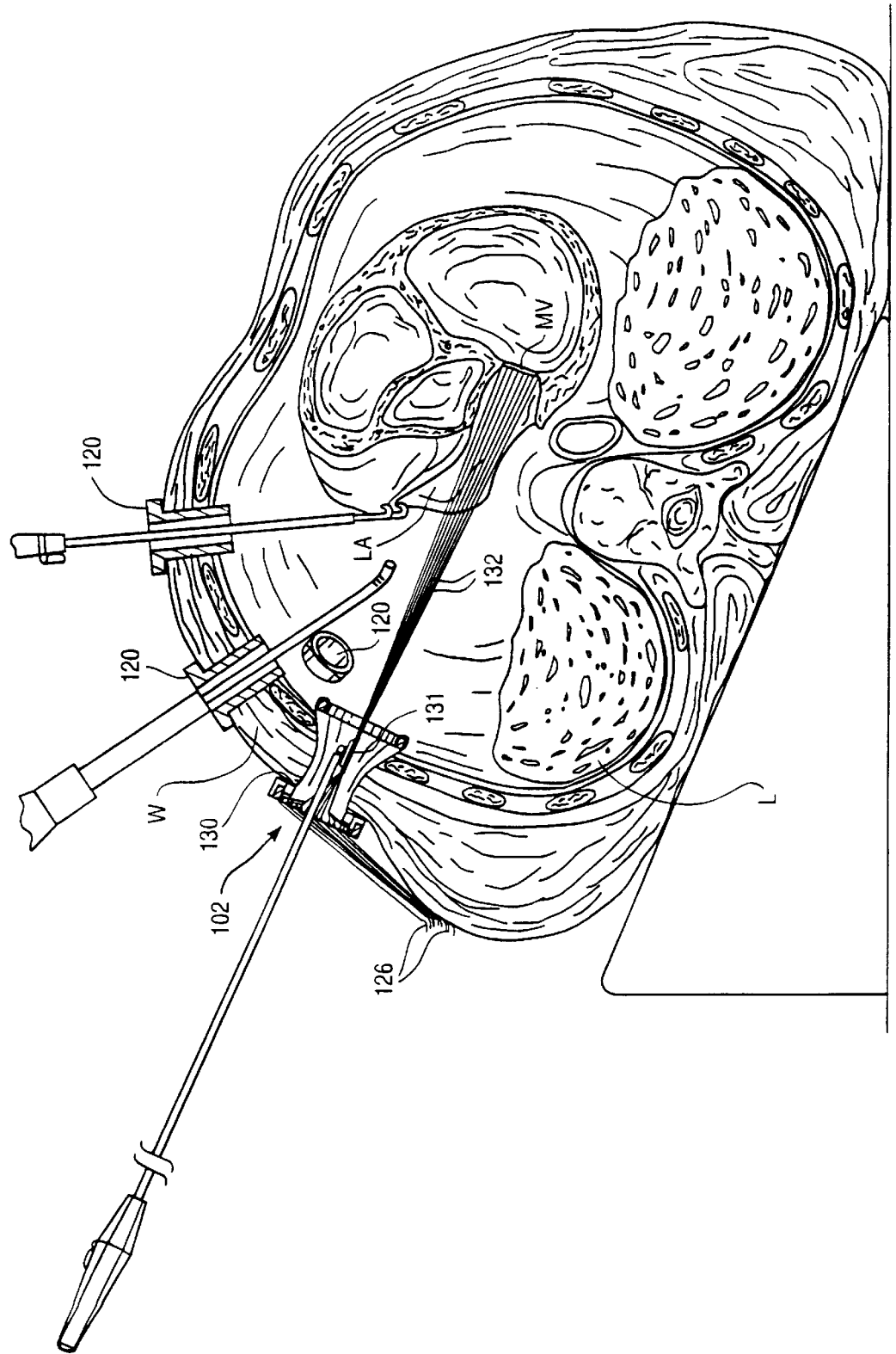
FIG. 13 illustrates a method of retracting tissue during treatment of cardiac valve disease, according to another embodiment of the present invention.
Figure 14:
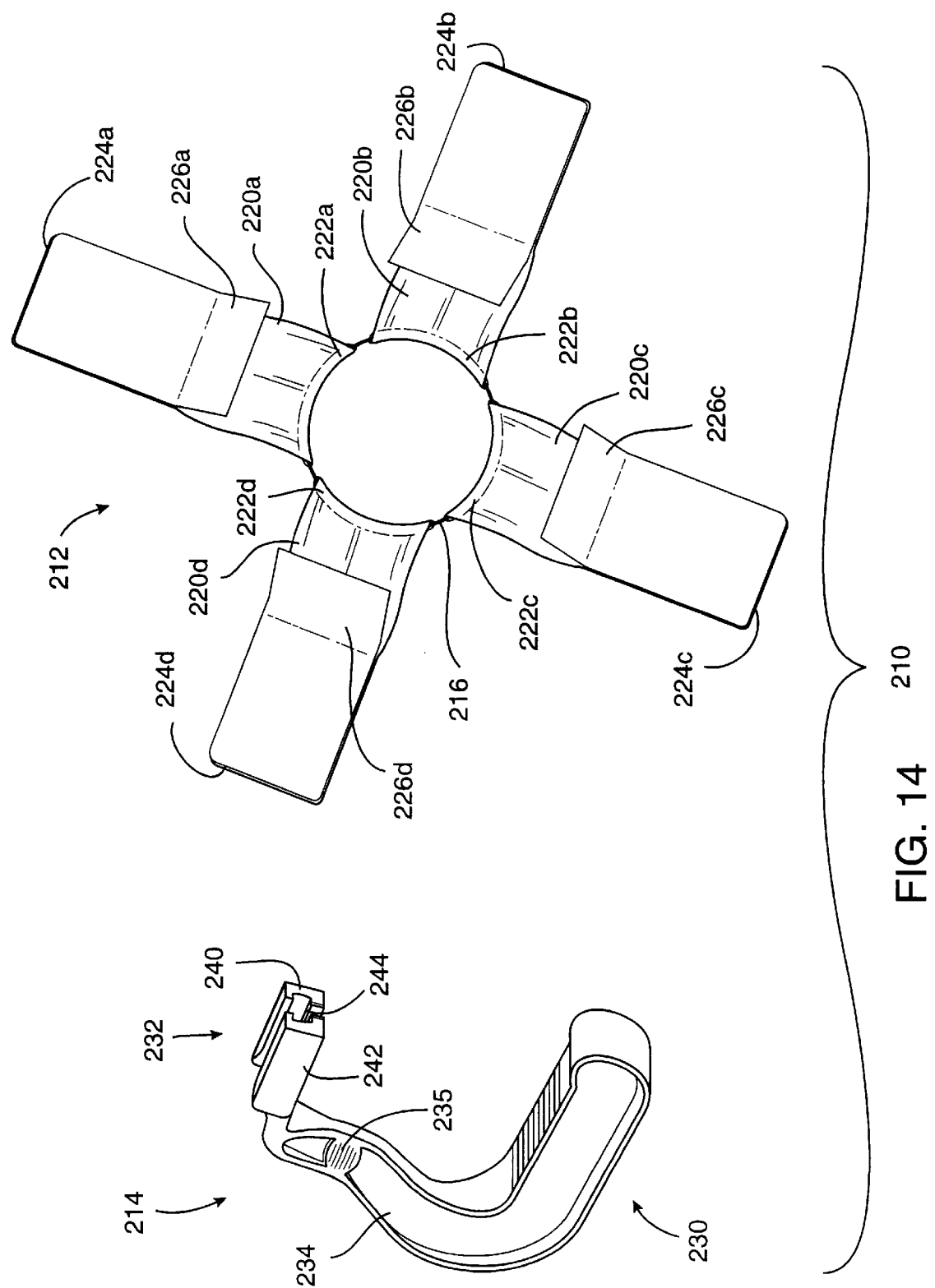
FIG. 14 illustrates a retractor system constructed according to another embodiment of the invention, the system including a retractor and an associated delivery device.

Referring now to FIG. 13, a retractor 130 similar to the embodiment shown in FIG. 10A and having suture organizing outer ring 102 as illustrated in FIG. 10F is particularly advantageous for use in a less invasive surgical procedure for repair or replacement of a heart valve, for example, a mitral valve MV via the left atrium LA. Access to the heart H through the window provided by retractor 130, and/or through trocar sheaths 120 is improved by deflating right lung L. As more fully explained in copending patent application Ser. No. 08/485,600, filed Jun. 7, 1995, which corresponds to PCT application WO 96/39942 published Dec. 19, 1996, the full disclosure of which is incorporated herein by reference, a valve prosthesis 131, such as a mechanical heart valve or annuloplasty ring, may be positioned through retractor 130 into the heart and secured at the native valve position to repair or replace the native valve. A plurality of sutures 132 are used to secure the prosthesis in the heart, and each suture may be drawn out of the chest and retained in suture organizing outer ring 102 as described above in connection with FIG. 10F to prevent tangling and disorganization.

With reference to FIGS. 14–24, a retractor system constructed according to another embodiment of the invention is indicated generally by the reference numeral 210 and includes a retractor 212 and a delivery device 214 for applying the retractor to a patient's body. The retractor 212 preferably is constructed as described above in connection with the embodiments illustrated in FIGS. 1–6. The retractor 212 comprises an anchoring frame which may be in the form of an anchoring ring 216. The anchoring ring 216 may be formed of the materials described above, and preferably a superelastic material, e.g., Nitinol. While a circular ring is illustrated, the anchoring frame may take various shapes and have either a continuous or discontinuous periphery. The anchoring ring 216 defines a central opening 218 and supports at least one, and preferably more than one, flexible tensioning member configured to retract tissue and hold the tissue in the retracted condition. The anchoring ring 216 can assume an expanded orientation (shown in FIG. 14–16) and a collapsed orientation (shown in FIGS. 17–19). The size of the anchoring frame and the flexible tensioning members of the retractor 212 may be varied for use in different applications or on different size patients.

The preferred flexible tensioning member comprises a plurality of flexible tabs 220a–220d having proximal ends 222a–222d and distal ends 224a–224d. The tabs 220a–220d may be formed of any suitable material, and preferably are formed from an absorbent material such as polyester nonwoven fabric. The proximal ends 222a–222d of the tabs are connected to, or alternatively formed integrally with, the anchoring ring 216 as discussed above with respect to previous embodiments. The tabs 220a–220d are provided with an attachment mechanism to secure the tabs in a position which maintains retraction of tissue away from the opening in the patient's body. In the preferred embodiment, the tabs 220a–220d carry adhesive on one surface for adhering the tabs to the patient's skin, or to sterile surgical film which is itself adhered to the patient's skin. The adhesive is covered by backing strips 226a–226d which may be removed after the retractor has been positioned within the patient's body. The tabs are tensioned to retract tissue and then adhered to the patient's body, thereby widening an opening in the patient's body.

The delivery device 214 for applying the retractor 212 to a patient's body has a proximal end in the form of a handle 230 and a distal end in the form of a retractor engaging portion 232 which is preferably generally parallel to and spaced from the handle. The handle 230 and the retractor engaging portion 232 are joined by a connecting member 234 which extends transversely to the axis of the handle. The member 234 is preferably substantially perpendicular to the handle 230 so as to give the device 214 a generally C-shaped configuration. While such configuration is preferred, those skilled in the art will appreciate that the shape of the device 214 may be varied from that illustrated. The delivery device 214 preferably is formed as an integral structure of any suitable material. For example, the device 214 may be molded from a fairly rigid thermoplastic such as polycarbonate or ABS. The device 214 could, however, be formed by securing different components together and, in addition, other materials of construction could be used.

The handle 230 of the device 214 is preferably formed so as to be easily gripped with one hand and may include ribs or other texturing to improve handling. The retractor engaging portion 232 of the device 214 is configured to releasably hold the retractor 212 in its collapsed orientation to facilitate placement of the retractor in the patient's body. As described below, once inside the patient's body, the device 214 is disengaged to allow the retractor 212 to assume its expanded orientation. The retractor engaging portion 232 includes first and second surfaces 236, 238 configured to engage the retractor 212. The retractor engaging surfaces 236, 238 are preferably substantially fixed in position with respect to the device 214.

In the preferred embodiment, the retractor engaging surfaces 236, 238 are defined on the interior of first and second channels 240, 242. The channels 240, 242 are preferably generally U-shaped in cross-section and face each other as shown in the Figures. The channels 240, 242 include, respectively, upper flanges 244, 246, lower flanges 248, 250, and central portions extending between the flanges. The first and second surfaces 236, 238 are preferably coextensive with and defined by the interior surfaces of, respectively, the channels 240, 242. The channels 240, 242 extend distally from the central connecting portion 234 of the delivery device 214 and are preferably separated by a slot 243 which acts as a means for guiding the retractor tabs 220a, 200c into the delivery device 214. The slot 243 permits a slight amount of relative movement of the channels 240, 242 toward or away from each other to facilitate loading of the retractor on the device 214; however, the position of each channel is preferably substantially fixed and immovable with respect to the handle 230 of the device. The channels 240, 242 are spaced by slot 243 a distance which allows the surfaces 236, 238 to receive and maintain the retractor 212 in its collapsed orientation. The slot 243 is sized so that the channels 240, 242 frictionally engage the tabs of retractor 212. This provides a controlled release of the retractor 212 from the device 214, i.e., the anchoring ring 216 does not spring open to its expanded orientation immediately upon disengagement from the device 214.

The channels 240, 242 also may be provided with a feature that allows the delivery device to be easily and quickly slid off of the retractor once same has been positioned in the patient's body. In the preferred and illustrated embodiment, the upper flanges 244, 246 of channels 240, 242 are tapered at their proximal ends 252, 254 to facilitate disengagement of the delivery device 214 from the retractor 212. The slot 243 preferably has a reduced size section 243a which frictionally engages the retractor tabs to prevent the anchoring ring 216 from springing open to its expanded orientation immediately upon disengagement. While the slot 243 has a larger section 243b, it could be of constant size along its length if desired.

Referring to FIG. 14A, the central portion of channel 240 extending between the upper and lower flanges 244, 248, and the central portion of channel 242 extending between the upper and lower flanges 246, 250, have interior surfaces 241, 243 which are preferably slightly radiused or concave. The anchoring ring 216 of retractor 212 moves into the concave central portions upon loading the retractor onto the device 214, which ensures proper engagement between the two components. Also, the upper flanges 244, 246 are undercut to provide surfaces 245, 247 which extend slightly upward away from the slot 243. This provides recessed areas which lock the anchoring frame 216 in the channels 240, 242 when the retractor 212 is loaded onto the delivery device 214. In addition, as shown in FIG. 14A, the lower flange 250 is undercut to provide surface 251 which extends slightly downward away from slot 243. This undercut portion catches the anchoring ring 216 upon fully loading the retractor 212 onto delivery device 214 to prevent the ring from sliding out of the channel 242.

Referring to FIG. 14B, it can be seen that in the preferred embodiment the distal ends of the lower flanges 248, 250 are provided with chamfered edges 253, 255 to form a guide that receives the tabs 220a, 220c when loading the retractor 212 onto the delivery device 214. Also, the upper flange 246 of the channel 242 is preferably provided with a chamfered edge 249 which extends along all or a portion of the length of the channel to aid in sliding the anchoring ring 216 into the channel upon fully loading the retractor 212 onto the delivery device 214. The delivery device 214 preferably is formed so that all corners and edges are rounded or smooth to minimize trauma upon inserting the retractor 212 into a patient.

Figure 16:
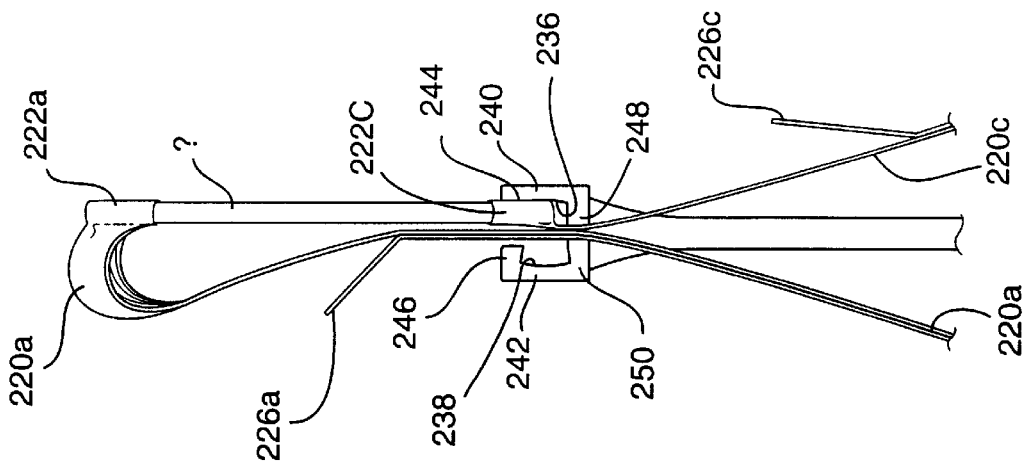
FIG. 16 is an end elevation view of the retractor system of FIG. 15, with portions of the retractor omitted for clarity.
Figure 15:
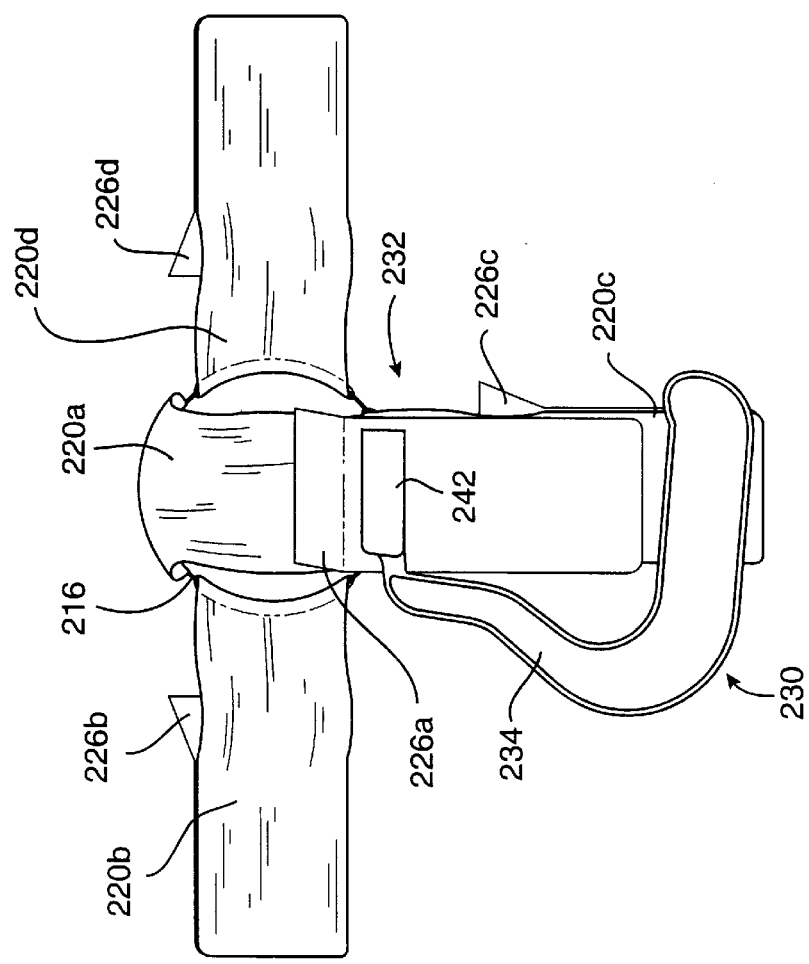
FIG. 15 is a side elevation view of the retractor system of FIG. 14, the retractor being partially loaded onto the delivery device.

FIG. 15 shows the retractor 212 after it has been partially loaded onto the delivery device 214. In order to load the retractor 212 onto the delivery device 214 to the extent shown in FIG. 15, the retractor 212 is rotated from the position of FIG. 14 such that the backing strips 226a–226d face away from the device. The tab 220a is folded back about the anchoring ring 216 toward the device 214 so as to overlie part of the tab 220c, which results in the backing strips 226a, 226c facing in opposite directions. The tabs 220a, 220c are then fed through the slot 243 between channels 240, 242 so as to position the portion of the anchoring ring 216 attached to the proximal end 222c of tab 220c within the channel 240, as shown in FIGS. 15 and 16. The retractor 212 can be placed in this position by sliding the tabs 220a, 220c in the slot 243 between the channels 240, 242, and then, if necessary, pulling the tab 220c toward the handle 230 to move the anchoring ring 216 into channel 240. The channels 240, 242 preferably can be flexed a limited amount to aid in passing the tabs 220a, 220c into the slot 243. As seen in FIG. 16, in which the tabs 220b, 220d have been omitted for clarity, the tabs 220a, 220c extend through the slot 243 to a location that is adjacent the handle 230.

In order to fully load the retractor 212 onto the delivery device 214, the tab 220a is pulled toward the handle 230 so as to move from the position shown in FIGS. 15 and 16 to the position shown in FIGS. 17–19. This pulls the anchoring ring 216 toward the handle 230, which causes the ring to assume its collapsed orientation as the portion of the ring attached to the proximal end 222a of tab 220a moves into the channel 242. See FIGS. 18 and 19, in which the tabs 220b, 220d have been omitted for clarity. In the collapsed orientation, the retractor 212 possesses a relatively narrow configuration to facilitate its introduction through an incision in the patient's body. The tabs 220a, 220c are preferably inserted into slot 243 so that the anchoring ring 216 assumes a narrow orientation on both ends thereof. That is, the anchoring ring 216 is configured such that it assumes a smaller profile when collapsed in the direction illustrated as opposed to an opposite direction perpendicular thereto.

The tab 220a may be provided with printing to indicate the manner in which it is manipulated to fully load the retractor 212 on the delivery device 214. For example, depending on the size of the retractor, and in particular the anchoring ring 216, it may be necessary to pull the tab down and toward the connecting portion 234 of device 214 to prevent the ring 216 and tabs from slipping out of the retractor engaging portion 232. Also, the connecting portion 232 of delivery device 214 may be provided with a gripping area 235 for holding the device 214 in one hand while pulling the tab.

Figure 20:
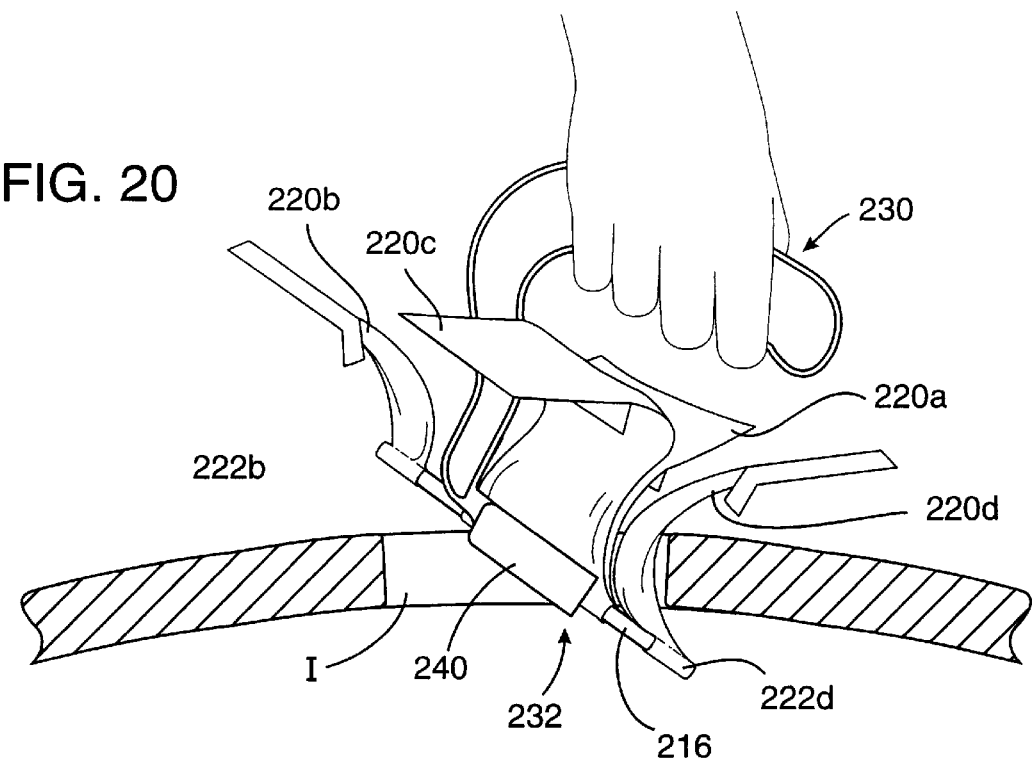
FIGS. 20–22 show in schematic fashion, respectively, inserting the retractor system of FIG. 17 into a patient's body, positioning the retractor within the patient's body, and removing the delivery device so that the retractor remains within the patient's body.
Figure 21:
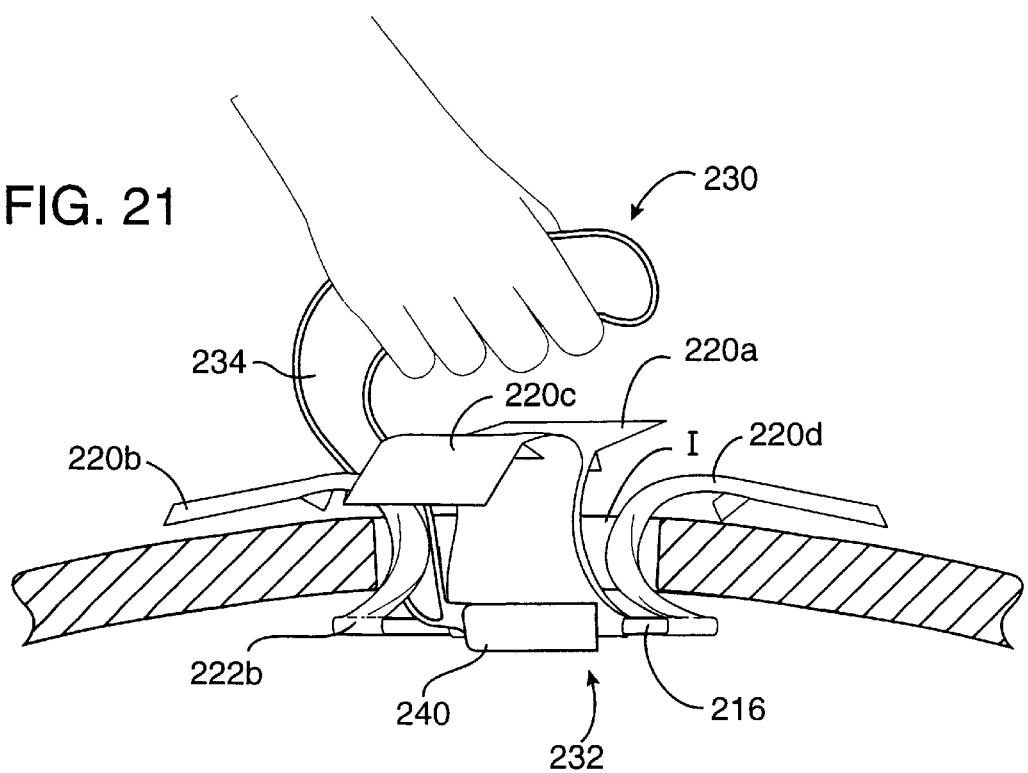
Figure 22:
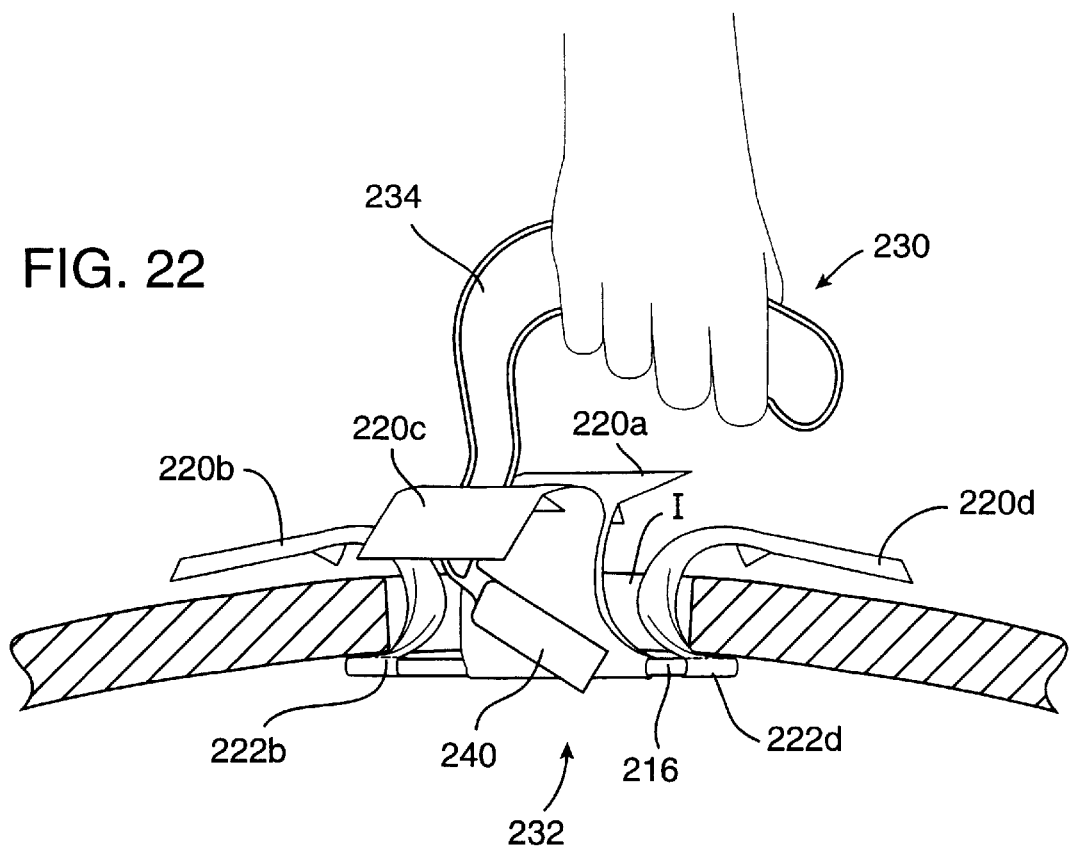

Referring to FIG. 20, once the retractor 212 in its collapsed orientation has been fully loaded onto the delivery device 214, the user grasps the handle 230 and inserts the front end of the device 214 into an incision I formed in a patient's body. In the exemplary application illustrated in FIGS. 20–23, the retractor 212 is being inserted into an incision in a patient's chest wall; however, those skilled in the art will appreciate that the invention may be used in various other applications. The flexible tabs 220a–220d do not interfere with inserting the retractor 212 and are easily moved away from the anchoring ring 216 so as to extend out of the patient's body. The front end of the retractor 212 is inserted toward one end of the incision I at an angle, thereby permitting the proximal end of the retractor to be moved past the other end of the incision. FIG. 21 shows the retractor 212 fully inserted into the patient's body, with the tabs 220a–220d extending from the anchoring ring 216 such that their adhesive coated surfaces and backing strips 226a–226d face the outer surface of the patient's body. In this position, the anchoring ring 216 is held in the channels 240, 242 so that the retractor 212 remains in its collapsed orientation.

In order to position the retractor 212 at a desired location within the patient's body, the delivery device 214 is moved laterally (to the left as viewed in FIG. 21) to position the back end of the device 214 against the end of the incision. This ensures that the retractor 212 is properly located under the chest wall. From this position, the handle 230 is lifted to raise the back end of the device 214 such that it pivots somewhat about the front end of the device 214. This causes the anchoring ring 216 to slide out of the tapered ends 252, 254 of channels 240, 242. The retractor is disengaged as the device 214 slides off the anchoring ring 216 and the tabs 220a, 220c. The anchoring ring 216 assumes its expanded orientation within the patient's body, and the tabs 220a–220d of retractor 212 are tensioned as described above, preferably in opposing fashion. The backing strips 226a–226d are removed from the tabs 220a–220d and each tab is secured to the patient's skin (or film covering the skin).

Figure 23:
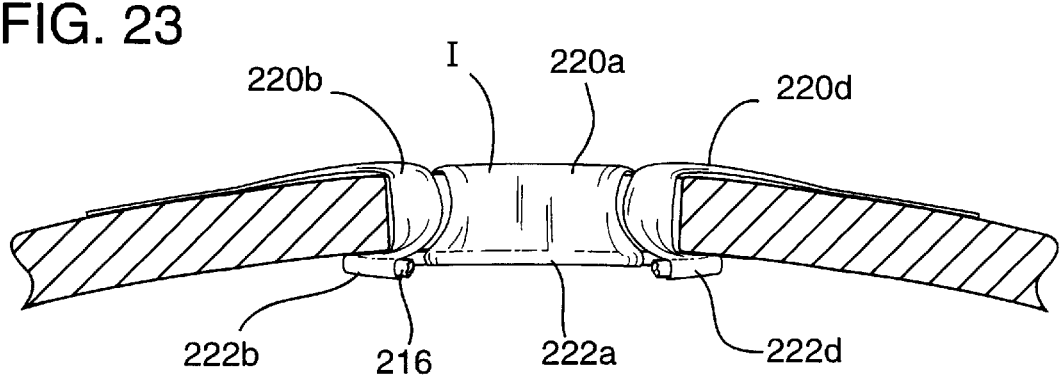
FIG. 23 shows the retractor of FIGS. 20–22 after it has been positioned and secured to the patient's body.

The resulting configuration is shown in FIG. 23, in which the tab 220c has been omitted for clarity. While the tabs 220a–220d are intended to be adhesively secured to the patient's skin, it will be appreciated that the tabs could be secured to the patient by other mechanisms, or could alternatively be secured to a support member located on or near the patient. The retractor 212 provides considerable access through an incision formed in the patient's body, for example, an incision in an intercostal space between adjacent ribs. The tabs 220a–220d can be manually tensioned a desired amount to retract tissue away from the incision and then secured in position, ensuring ample access to the patient's body cavity.

Figure 24:
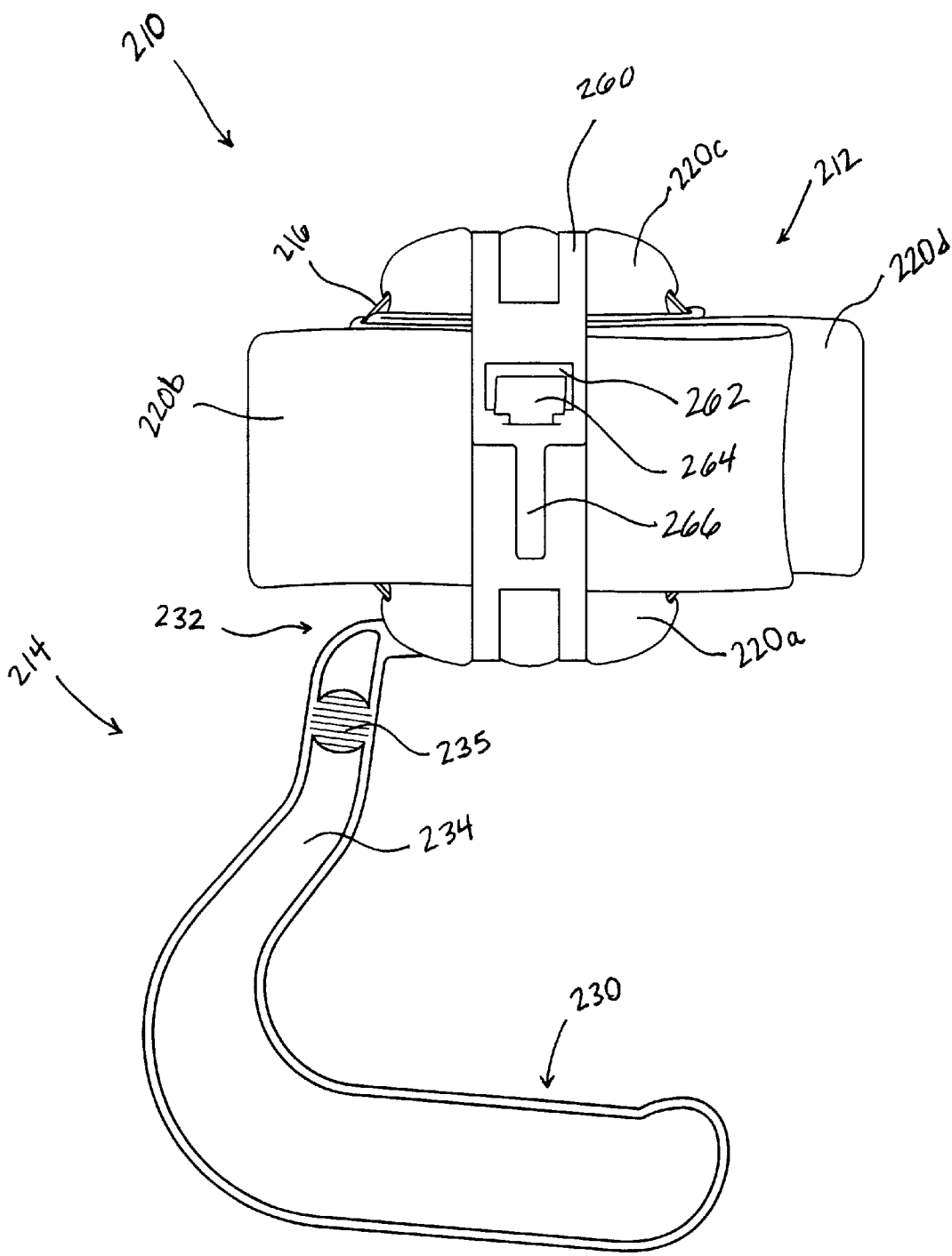
FIG. 24 is a front elevation view of the retractor system of FIG. 14 showing the retractor partially loaded onto the delivery device according to another embodiment of the invention.

The delivery device 214 and retractor 212 provide a system which is simple to use and facilitates quick and easy placement of the tissue retractor in a patient's body. The retractor 212 may be supplied partially loaded onto the delivery device 214 in sterile condition. For example, as shown in FIG. 24, the tabs 220a–220d may be folded onto the anchoring ring 216 and secured in position by a suitable fastener, such as a tie strap 260. The illustrated tie strap 260 comprises an elongated band formed of any suitable material, such as plastic, which has an opening 262 at one end which removably receives a locking tab 264. A pull tab 266 is provided to remove the strap 260 and may be provided with printing to indicate the manner in which it should be removed. The system 210 as illustrated in FIG. 24 may be packaged and sterilized in any conventional manner, for example, by E-beam irradiation. At the point of end use, the system is removed from the package and the tie strap 260 is removed. The tabs 220a–220d are then unfolded, and one of the tabs is pulled to collapse the anchoring ring 216 and fully load the retractor 212 onto the device 214, for example, as shown in FIGS. 17–19. The retractor 212 is then inserted into the patient's body, the delivery device 214 is removed, and the tabs 220a–220d are adhered to the patient, as described above.

Although the invention has been described in some detail by way of illustration and example for purposes of making a complete disclosure, certain changes and modifications will be apparent to those skilled in the art. For example, both the outer ring and the anchoring frame structures may take a variety of forms, including articulated linkages, expandable balloons, multiple layer coils, and the like. Thus, the scope of the present invention is limited solely by the following claims.

What is claimed is:

1. A retractor system comprising:
a retractor comprising an anchoring frame and at least one flexible tensioning member extending from the anchoring frame, the flexible tensioning member adapted to be tensioned to widen an incision in the patient's body, wherein the retractor can assume collapsed and expanded orientations; and
a delivery device comprising a handle and a retractor engaging portion including first and second retractor engaging surfaces configured to hold the retractor in said collapsed orientation, wherein the retractor engaging portion of the delivery device is releasable from the retractor without moving the first and second retractor engaging surfaces relative to each other to allow the retractor to assume said expanded orientation in the patient's body.

2. The system of claim 1, wherein the retractor engaging portion comprises first and second channels respectively defining said first and second retractor engaging surfaces, and wherein the first and second channels are separated by a slot adapted to guide the at least one flexible tensioning member of the retractor into the retractor engaging portion of the delivery device.

3. The system of claim 2, wherein each of the first and second channels includes a central portion disposed between upper and lower flanges, the central portion and upper and lower flanges of each channel defining one of said retractor engaging surfaces.

4. The system of claim 3, wherein the first and second channels have a tapered portion to facilitate release of the delivery device from the retractor.

5. The system of claim 1, wherein the anchoring frame comprises a ring formed of a superelastic material, and the at least one flexible tensioning member comprises a plurality of flexible tabs secured to the ring.

6. The system of claim 5, wherein each of the plurality of flexible tabs has an adhesive coating for securing the tab to the patient's body.

7. The system of claim 1, wherein the delivery device is a one-piece member free of moving parts.

8. A device for applying a retractor to a patient's body, the device comprising:
a handle having an axis; and
a retractor engaging portion coupled to the handle, the retractor engaging portion including first and second surfaces configured to engage a retractor;
wherein the retractor engaging portion is spaced from and generally parallel to the axis of the handle and is coupled to the handle by a connecting member which is disposed transverse to the axis of the handle.

9. The device of claim 8, wherein the retractor engaging portion includes first and second channels which respectively define the first and second surfaces.

10. The device of claim 9, wherein the first and second channels are generally U-shaped and face toward each other.

11. The device of claim 9, wherein the first and second channels are separated by a slot which permits limited flexing of the first and second channels toward or away from each other.

12. The device of claim 9, wherein each of the first and second channels defines a flange having a proximal end and a distal end, and the proximal end of each flange is tapered to disengage the first and second channels from a retractor.

13. The device of claim 8, wherein the handle and the retractor engaging portion are formed as a one-piece member.

14. The device of claim 8, wherein the device is molded from rigid plastic material.

15. The device of claim 8, wherein the retractor engaging portion is provided with means for guiding a retractor into engagement therewith.

16. The device of claim 8, wherein the connecting member is generally perpendicular to the axis of the handle and the device is generally C-shaped.

17. A sterilized medical kit comprising:
a retractor movable between collapsed and expanded orientations, the retractor including an anchoring frame and at least one flexible tensioning member; and
a device for placing the retractor in a patient's body when the retractor is in said collapsed orientation;
wherein the retractor and the device are contained in a sealed package which maintains the retractor and the device in sterile condition.

18. A method of loading a surgical retractor onto a delivery device adapted to deliver the retractor into an incision formed in a patient's body, the method comprising steps of:
providing a retractor including an anchoring frame and at least one flexible tensioning member extending away from the anchoring frame, wherein the anchoring frame is collapsible and can assume collapsed and expanded orientations;

providing a delivery device including a handle configured to be grasped by a user and a retractor engaging portion configured to support the retractor in said collapsed orientation; and loading the retractor onto the retractor engaging portion of the delivery device in said collapsed orientation by moving the retractor relative to the delivery device.

19. The method of claim 18, wherein the loading step is performed by first placing the retractor in said expanded configuration in the retractor engaging portion of the delivery device, and then deforming the anchoring frame to place the retractor in said collapsed orientation.

20. The method of claim 19 wherein the loading step is performed by placing part of the anchoring frame of the retractor in said expanded configuration in the retractor engaging portion of the delivery device, and then moving the at least one flexible tensioning member with respect to the delivery device to deform the anchoring frame to place the retractor in said collapsed orientation.

21. A method of positioning a surgical retractor in a patient's body, the method comprising steps of:

providing a retractor including an anchoring frame and at least one flexible tensioning member extending away from the anchoring frame, wherein the anchoring frame is collapsible and can assume collapsed and expanded orientations;

loading the retractor onto a delivery device having a retractor engaging portion which holds the retractor in said collapsed orientation;

inserting the delivery device into an incision in a patient's body until the anchoring frame and at least part of the at least one flexible tensioning member are disposed within the patient's body; and removing the retractor engaging portion of the delivery device from the retractor while the retractor is in said collapsed orientation to allow the retractor to thereafter assume said expanded orientation within the patient's body.

22. The method of claim 21 wherein the retractor engaging portion of the delivery device includes a pair of channels which maintain the retractor in said collapsed orientation until the retractor engaging portion of the delivery device is removed from the retractor.

23. The method of claim 22 wherein the retractor engaging portion of the delivery device includes a pair of channels each having a tapered portion, and the removing step is performed by moving the retractor engaging portion of the delivery device with respect to the retractor such that the retractor slides out of the tapered portions of the channels.

24. The method of claim 23 wherein adhesive is provided on the at least one flexible tensioning member, and further comprising the step of tensioning and securing the at least one tensioning member to the patient's body.

25. A tissue retractor system for providing surgical access through an incision in tissue to a body cavity of a patient, the system comprising:

a retractor comprising:

an anchoring frame having an opening, the frame being movable from a narrow profile, which facilitates insertion through an incision into a body cavity, to a wide profile, the wide profile being wider than the narrow profile, the frame being biased to the wide profile;

a flexible tensioning member extending from the frame adjacent to the opening, said tensioning member being selectively tensionable to spread the tissue adjacent to the incision and being adapted to be secured in tension; and a retractor delivery device including a device body having a distal end and a proximal end, the delivery device releasably holding the frame in the narrow profile for introduction into a patient.

26. A tissue retractor system as claimed in claim 25 wherein the frame is resiliently expandable from the narrow profile into the wide profile configuration.

27. A tissue retractor system as claimed in claim 26, wherein the delivery device includes a handle having an actuator for releasing the frame in the narrow profile.

28. A tissue retractor system as claimed in claim 27, wherein actuation of the actuator enlarges a gap between the inward facing surfaces.

29. A tissue retractor system as claimed in claim 28, wherein the delivery device includes a pair of inward facing surfaces disposed on a pair of generally U-shaped arms at the distal end of the device body.

30. A tissue retractor system as claimed in claim 25, further comprising an outer frame structure to which the tensioning member may be attached to maintain the tensioning member in tension.

31. A tissue retractor system as claimed in claim 27, wherein actuation of the handle slides the frame distally relative to the inward facing surfaces.

32. A tissue retractor system as claimed in claim 26, wherein a tether extends from the tensioning member to the delivery device.

33. A tissue retractor system as claimed in claim 30, wherein the outer frame structure is expandable to apply tension to the tensioning member.

34. A tissue retractor system as claimed in claim 30, further comprising a plurality of clasps for attaching the tensioning member to the outer frame structure.

35. A tissue retractor delivery device for use with a retractor comprising an anchoring frame restrainable into a narrow profile for insertion through an incision into a body cavity, the frame expandable to a wide profile wider than the incision and having an opening, a tensioning member extending from the frame adjacent to the opening, the tensioning member being selectively tensionable to spread tissue outward from the incision so as to provide surgical access into the body cavity, the delivery device comprising:

a device body having distal and proximal ends;

a pair of inward facing surfaces near the distal end which restrain the frame to the small profile;

a handle near the proximal end for supporting the inward facing surfaces; and an actuator on the handle for effecting expansion of the frame to the wide profile within the body cavity.

36. A delivery device as claimed in claim 35, wherein actuation of the actuator increases a gap between the inward facing surfaces.

37. A tissue retractor system as claimed in claim 36, wherein the inward-facing surfaces are disposed on a pair of generally U-shaped arms extending from the proximal end of the device body.

* * * * *